(12) United States Patent
Yun et al.

(10) Patent No.: US 11,338,120 B2
(45) Date of Patent: May 24, 2022

(54) METHODS AND DEVICES FOR TREATING PARASYMPATHETIC BIAS MEDIATED CONDITIONS

(71) Applicant: Palo Alto Investors LP, Palo Alto, CA (US)

(72) Inventors: Anthony Joonkyoo Yun, Menlo Park, CA (US); Jeremy Thomas Yun, Menlo Park, CA (US); Eric Foster Yun, Menlo Park, CA (US)

(73) Assignee: Palo Alto Investors LP, Palo Alto, CA (US)

( * ) Notice: Subject to any disclaimer, the term of this patent is extended or adjusted under 35 U.S.C. 154(b) by 105 days.

(21) Appl. No.: 16/384,347

(22) Filed: Apr. 15, 2019

(65) Prior Publication Data

US 2019/0240468 A1    Aug. 8, 2019

Related U.S. Application Data

(63) Continuation-in-part of application No. 14/012,771, filed on Aug. 28, 2013, now Pat. No. 10,426,950.

(60) Provisional application No. 61/772,403, filed on Mar. 4, 2013, provisional application No. 61/762,223, filed on Feb. 7, 2013, provisional application No. 61/694,630, filed on Aug. 29, 2012.

(51) Int. Cl.

| | | |
|---|---|---|
| *A61M 37/00* | (2006.01) | |
| *A61H 1/00* | (2006.01) | |
| *A61N 7/00* | (2006.01) | |
| *A61N 5/06* | (2006.01) | |
| *A61N 1/36* | (2006.01) | |

(52) U.S. Cl.
CPC .......... *A61M 37/0015* (2013.01); *A61H 1/00* (2013.01); *A61N 1/3605* (2013.01); *A61N 1/3606* (2013.01); *A61N 1/36014* (2013.01); *A61N 1/36017* (2013.01); *A61N 5/0622* (2013.01); *A61N 7/00* (2013.01); *A61M 2037/0023* (2013.01); *A61N 1/36085* (2013.01); *A61N 1/36167* (2013.01); *A61N 2005/0659* (2013.01); *A61N 2005/0663* (2013.01); *A61N 2007/0026* (2013.01)

(58) Field of Classification Search
CPC .... A61N 5/0622; A61N 7/00; A61N 1/36017; A61N 1/00; A61N 1/36014; A61N 1/3605; A61N 1/3606; A61N 1/36085; A61N 2005/0659; A61N 2005/0663; A61N 1/36167; A61N 2007/0026; A61M 37/0015; A61M 37/0092; A61M 2037/0023; A61B 5/486; A61B 5/0484; A61B 5/14532; A61B 5/0816; A61B 5/0402; A61B 5/02416; A61B 5/14542; A61H 1/00

See application file for complete search history.

(56) References Cited

U.S. PATENT DOCUMENTS

| | | |
|---|---|---|
| 5,413,550 A | 5/1995 | Castel |
| 7,149,574 B2 | 12/2006 | Yun et al. |
| 7,177,686 B1 * | 2/2007 | Turcott ............. A61B 5/02405 600/485 |
| 7,200,443 B2 | 4/2007 | Faul |
| 7,283,861 B2 | 10/2007 | Bystritsky |
| 7,363,076 B2 | 4/2008 | Yun et al. |
| 7,711,430 B2 | 5/2010 | Errico et al. |
| 7,738,952 B2 | 6/2010 | Yun et al. |
| 7,899,527 B2 | 3/2011 | Yun et al. |
| 8,428,738 B2 | 4/2013 | Valencia |
| 8,440,632 B2 | 5/2013 | Kullok et al. |
| 8,517,911 B1 | 8/2013 | Thompson |
| 8,569,277 B2 | 10/2013 | Yun et al. |
| 8,571,650 B2 | 10/2013 | Yun |
| 8,715,209 B2 * | 5/2014 | Gertner .................... A61B 8/06 601/3 |
| 8,908,641 B2 | 12/2014 | Qi et al. |
| 9,457,166 B1 | 10/2016 | Lasorso, Jr. |
| 9,480,812 B1 | 11/2016 | Thompson |
| 10,010,713 B2 | 7/2018 | Lin |
| 10,155,114 B2 | 12/2018 | De Ridder |
| 2004/0249416 A1 | 12/2004 | Yun et al. |
| 2005/0021092 A1 | 1/2005 | Yun et al. |
| 2005/0143378 A1 | 6/2005 | Yun et al. |
| 2005/0143788 A1 | 6/2005 | Yun et al. |
| 2005/0153885 A1 | 7/2005 | Yun et al. |
| 2005/0240241 A1 | 10/2005 | Yun et al. |
| 2005/0256028 A1 | 11/2005 | Yun et al. |
| 2006/0116721 A1 | 6/2006 | Yun et al. |
| 2007/0203432 A1 | 8/2007 | McNew |

(Continued)

OTHER PUBLICATIONS

Wegrzyn et al. Work Group report: Oral food challenge testing. Journal of Allergy and Clinical Immunology (2009), 123 (6:suppl.), S365-S383 (Year: 2009).*

(Continued)

*Primary Examiner* — Sean C. Barron
(74) *Attorney, Agent, or Firm* — Peter W. Schroen; Bret E. Field; Bozicevic, Field & Francis LLP

(57) ABSTRACT

Methods for treating a subject for a parasympathetic bias mediated condition are provided. Aspects of the methods include modulating at least a portion of the subject's autonomic nervous system to increase the sympathetic/parasympathetic activity ratio in a manner effective to treat the subject for the parasympathetic bias mediated condition. In some instances, the subject is known to have parasympathetic bias. Also provided are devices that find use in practicing various embodiments of the methods.

17 Claims, No Drawings

(56) References Cited

U.S. PATENT DOCUMENTS

| | | | |
|---|---|---|---|
| 2009/0171418 A1* | 7/2009 | Sarif | A61H 39/002 607/59 |
| 2010/0119482 A1 | 5/2010 | Yun et al. | |
| 2010/0144691 A1 | 6/2010 | Yun et al. | |
| 2010/0260669 A1 | 10/2010 | Yun et al. | |
| 2010/0286734 A1 | 11/2010 | Yun et al. | |
| 2011/0112394 A1 | 5/2011 | Mishelevich | |
| 2011/0130615 A1 | 6/2011 | Mishelevich | |
| 2011/0178442 A1 | 7/2011 | Mishelevich | |
| 2011/0190668 A1 | 8/2011 | Mishelevich | |
| 2011/0208094 A1 | 8/2011 | Mishelevich | |
| 2012/0270876 A1 | 10/2012 | Yun et al. | |
| 2012/0283502 A1 | 11/2012 | Mishelevich et al. | |
| 2013/0053817 A1 | 2/2013 | Yun | |
| 2014/0343463 A1 | 11/2014 | Mishelevich | |
| 2016/0262974 A1 | 9/2016 | Mirzai et al. | |
| 2016/0310315 A1 | 10/2016 | Smith | |
| 2017/0080255 A1 | 3/2017 | Law et al. | |
| 2018/0117017 A1 | 5/2018 | Nemechek | |
| 2019/0001135 A1 | 1/2019 | Yoo et al. | |
| 2019/0069842 A1* | 3/2019 | Rothberg | A61B 8/429 |

OTHER PUBLICATIONS

Wieling et al. Prolonged post-faint hypotension can be reversed by dynamic tension. Clin Auton Res (Jul. 2011), 21, 415-418. (Year: 2011).*

Kurowski et al. Food Allergies: Detection and Management. American Family Physician (2008), 77(12), 1678-1686. (Year: 2008).*

Hirschowitz et al. Anticholinergic Potency of Diphenhydramine (Benadryl) Measured against Bethanechol in the Gastric Fistula Dog The Journal of Pharmacology and Experimental Therapeutics (1983), 226(1), 171-173. (Year: 1983).*

About food allergies, treating and managing reactions, Retrieved from http://www.foodallergy.org/treating-an-allergic-reaction.

Adrenaline (epinephrine). (2006). In Churchill Livingstone's dictionary of nursing. Philadelphia, PA: Elsevier Health Sciences. Retrieved from http://search.credoreference.com/content/entry/ehscldictnursing/adrenaline_epinephrine/0.

Anaphylaxis (2011). Internet Article, 3 pages.

Artificial Pacemaker (2008). Interent article, 1 page.

Bradycardia. (2005) I R. Youngson, Collins Dictionary of medicine. London, UK: Collins. Retrieved from http://search.credoreference.com/content/entry/collinsmed/bradycardia/0.

Heart Rate Variability Monitor For Patient Assessment and Treatment. Internet Article by BioCom Technologies, 1 page. (Year: 2009).

Aydin et al., Management and therapy of vasovagal syncope: A review, World J Cardiol. Oct. 26, 2010; 2(10): 308-315.

Basso et al., Neural correlates of IgE-mediated food allergy, J Neuroimmunol. Jul. 2003;140(1-2):69-77.

Belza et al., Bioactive food stimulants of sympathetic activity: effect on 24-h energy expenditure and fat oxidation, Eur J Clin Nutr. Jun. 2005;59(6):733-41.

Bock et al., Fatalities due to anaphylactic reactions to foods, J Allergy Clin Immunol. Jan. 2001;107(1):191-3.

Bray et al., Reciprocal relation of food intake and sympathetic activity: experimental observations and clinical implications, Int J Obes Relat Metab Disord. Jun. 2000;24 Suppl 2:S8-17.

Brignole, Vasovagal syncope and vasovagal disease, Hellenic J Cardiol. Mar.-Apr. 2008;49(2):61-4.

De Luca et al., A correlation between food allergy, the autonomic nervous system and the central nervous system: a study of 8 patients in childhood, Pediatr Med Chir. 996 Nov.-Dec.;18(6):565-71.

Fiocchi et al., World Allergy Organization (WAO) Diagnosis and Rationale for Action against Cow's Milk Allergy (DRACMA) Guidelines, Pediatr Allergy Immunol. Jul. 2010;21 Suppl 21:1-125.

Fleming et al., Normal ranges of heart rate and respiratory rate in children from birth to 18 years of age: a systematic review of observational studies, Lancet. Mar. 19, 2011;377(9770):1011-8.

Fukutomi et al.,. Abnormal responses of the autonomic nervous system in food-dependent exercise-induced anaphylaxis, Ann Allergy. May 1992;68(5):438-45.

Grassi et al., Essential hypertension and the sympathetic nervous system, Neurol Sci. May 2008;29 Suppl 1:S33-6.

Jardine et al., Autonomic control of vasovagal syncope, Am J Physiol. Jun. 1998;274(6):H2110-5.

Lenard et al., Central and peripheral regulation of food intake and physical activity: pathways and genes, Obesity (Silver Spring). Dec. 2008;16 Suppl 3:S11-22.

Liang et al., Vagal activities are involved in antigen-specific immune inflammation in the intestine, J Gastroenterol Hepatol Jun. 2011;26(6):1065-71.

McClain et al., Animal models of food allergy: opportunities and barriers, Curr Allergy Asthma Rep. Mar. 2006;6(2):141-4.

Miller et al., Depressed children with asthma evidence increased airway resistance: "vagal bias" as a mechanism? J Allergy Clin Immunol. Jul. 2009;124(1):66-73.e1-10.

Occhetta et al., Closed loop stimulation in prevention of vasovagal syncope. Inotropy Controlled Pacing in Vasovagal Syncope (INVASY): a multicentre randomized, single blind, controlled study, Europace. Nov. 2004;6(6):538-47.

Permaul et al., Anaphylaxis in a Patient with Long QT Syndrome. J Allergy Clin Immunol (2007), Abstract 132. (Year: 2007).

Ruiter et al., Permanent cardiac pacing for neurocardiogenic syncope, Neth Heart J. Oct. 2008; 16(Suppl 1): S15-S19.

Sicherer et al., American Academy of Allergy, Asthma & Immunology, Feb. 2010 vol. 125, Issue 2, Supplement 2, pp. S116-S125.

Simons et al., EpiPen Jr versus EpiPen in young children weighing 15 to 30 kg at risk for anaphylaxis, J Allergy Clin Immunol. Jan. 2002;109(1):171-5.

Vesalainen et al., Vagal cardiac activity in essential hypertension: the effects of metoprolol and ramipril, Am J Hypertens. Jun. 1998;11(6 Pt 1):649-58.

Yokusoglu et al., Heart rate variability in patients with allergic rhinitis, Mil Med. Jan. 2007;172(1):98-101.

Chanes et al., Causal Frequency-Specific Contributions of Frontal Spatiotemporal Patterns Induced by Non-Invasive Neurostimulation to Human Visual Performance, Journal of Neuroscience Mar. 13, 2013, 33 (11) 5000-5005.

Dakin et al., Frequency-specific modulation of vestibular-evoked sway responses in humans, J Neurophysiol. Feb. 2010;103(2):1048-56.

Feurra et al., Frequency Specific Modulation of Human Somatosensory Cortex, Front Psychol. 2011; 2: 13.

Russo et al., The physiological effects of slow breathing in the healthy human, Breathe (Sheff). Dec. 2017; 13(4): 298-309.

Zygmunt et al., Methods of evaluation of autonomic nervous system function, Arch Med Sci. Mar. 1, 2010; 6(1): 11-18.

* cited by examiner

METHODS AND DEVICES FOR TREATING PARASYMPATHETIC BIAS MEDIATED CONDITIONS

CROSS REFERENCE TO RELATED APPLICATIONS

The present application is a continuation-in-part of U.S. application Ser. No. 14/012,771, filed Aug. 28, 2013, which application claims priority to the filing date of U.S. Provisional Application Ser. No. 61/772,403 filed on Mar. 4, 2013; U.S. Provisional Application Ser. No. 61/762,223 filed Feb. 7, 2013; and U.S. Provisional Application Ser. No. 61/694,630 filed on Aug. 29, 2012; the disclosures of which applications are herein incorporated by reference.

INTRODUCTION

There are a variety of conditions that can affect an individual's health and well-being. The treatment of various conditions that affect the health and well-being of an individual has been around for centuries. Such treatments include pharmacological, surgical, and life style (dietetic, exercise, etc.) changes. In general, the armament of treatment options available to a physician to treat such conditions has increased tremendously, especially in the last century.

However, while the number of treatment options has increased, typically such options are merely palliative, i.e., are designed for the relief of symptoms of a condition rather than actually being curative of the disorder itself. In fact, treatment protocols effectively directed at the underlying cause of a condition are quite rare.

As such, there continues to be an interest in the development of new protocol options for treating conditions. Of particular interest are protocols for treating conditions that are directed at the cause of the condition rather than the symptoms thereof.

SUMMARY

Methods for treating a subject for a parasympathetic bias mediated condition are provided. Aspects of the methods include modulating at least a portion of the subject's autonomic nervous system to increase the sympathetic/parasympathetic activity ratio in a manner effective to treat the subject for the parasympathetic bias mediated condition. In some instances, the subject is known to have parasympathetic bias. Also provided are devices that find use in practicing various embodiments of the methods.

DETAILED DESCRIPTION

Methods for treating a subject for a parasympathetic bias mediated condition are provided. Aspects of the methods include modulating at least a portion of the subject's autonomic nervous system to increase the sympathetic/parasympathetic activity ratio in a manner effective to treat the subject for the parasympathetic bias mediated condition. In some instances, the subject is known to have parasympathetic bias. Also provided are devices that find use in practicing various embodiments of the methods.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

In further describing the invention, aspects of embodiments of methods of the invention are described first in greater detail, followed by a review of examples of applications in which the subject methods find use, as well as a description of representative devices which find use in practicing various embodiments of the methods.

Methods

Parasympathetic Bias Mediated Conditions

As summarized above, aspects of the invention include methods of treating a subject for a parasympathetic bias mediated condition. Parasympathetic bias mediated conditions are physiological conditions having one or more undesirable symptoms, where the symptoms arise (at least in part) from parasympathetic bias (at least in a portion of the subject's autonomic nervous system). Parasympathetic bias mediated conditions include both chronic and acute conditions. In some instances, the conditions of interest are disease conditions. In some instances, the conditions of interest are conditions arising in response to one or more stimuli, e.g., ingestion of nutritional or therapeutic compositions, exposure to certain environmental conditions, infection with a pathogenic agent, induction of stress, e.g., from exercise, etc. Examples of specific conditions of interest are provided in greater detail below.

Autonomic Function Modulation

Aspects of methods of the invention include treating a subject for a parasympathetic bias mediated condition by modulating autonomic function in the subject. By "modulating" is meant altering or changing one aspect or component to provide a change, alteration or shift in another aspect or component. Modulating autonomic function is achieved by modulating at least one portion of the subject's autonomic nervous system. By "modulating at least one portion of the subject's autonomic nervous system" is meant altering or changing at least a portion of an autonomic nervous system by a means to provide a change, alteration or shift in at least one component or aspect of the autonomic nervous system.

Methods of modulating at least one portion of the subject's autonomic nervous system according to certain embodiments include modulating the parasympathetic and/or sympathetic activity in the subject. "Parasympathetic activity" refers to activity of the parasympathetic nervous system whereas "sympathetic activity" refers to activity of the sympathetic nervous system. Also, as used herein, "activity" and "function" are used interchangeably. In some embodiments, methods include at least one of decreasing parasympathetic activity and or increasing sympathetic activity in a subject.

A subject's autonomic nervous system may be modulated using any convenient protocol, including energy-application protocols, pharmacologic protocols, and/or behavioral protocols. As such, embodiments of the subject methods include modulating at least one portion of the subject's autonomic nervous system to treat a subject for a target condition by administering an effective amount of a pharmacological agent and/or applying an appropriate energy to the subject. Pharmacologically modulating at least a portion of a subject's autonomic nervous system is also herein referred to as modulating the autonomic nervous system by utilizing a "pharmacological protocol". Energetically modulating at least a portion of a subject's autonomic nervous system is also herein referred to as modulating the autonomic nervous system by utilizing an "energy-application protocol". Behaviorally modulating at least a portion of a subject's autonomic nervous system is also herein referred to as modulating the autonomic nervous system by utilizing a "behavioral protocol". The pharmacological, energetic, and/or behavioral modulation may provide an increase in function of at least a portion of the autonomic system, e.g., increase function in at least one sympathetic nerve fiber, and/or provide a decrease in function or dampening of a portion of the autonomic system, e.g., may inhibit activity in at least one parasympathetic nerve fiber or inhibit nerve pulse transmission.

The pharmacological, energetic and/or behavioral modulation may be systemic or regional (i.e., localized). In other words, the entire autonomic nervous system may be modulated (e.g., the entire sympathetic nervous system and/or parasympathetic nervous system may be modulated) or only a portion of the autonomic nervous system may be modulated (e.g., only a portion of the sympathetic nervous system and/or parasympathetic nervous system may be modulated). Localization may be with respect to a particular area, organ, e.g., lung, or even to a particular nerve fiber. For example, localization may be with respect to innervations of one or more organs. Area(s) of the autonomic nervous system may include, but are not limited to, preganglionic and postganglionic nerve fibers, ganglionic structures, efferent and afferent nerve fibers, the hypothalamus, receptors on the hypothalamus, afferent autonomic nerves (sympathetic and parasympathetic) and hormonal receptors on the hypothalamus. In certain embodiments, a given nerve fiber or the like may be modulated with respect to sympathetic and/or parasympathetic activity in more than one area of the nerve fiber.

In some instances, the modulation that is achieved in practicing methods of the invention may be quantified. One way of quantifying modulation of at least one portion of the subject's autonomic nervous system is the parasympathetic/sympathetic activity ratio. By "parasympathetic/sympathetic activity ratio" is meant the ratio of activity of the sympathetic nervous system to the activity of the parasympathetic nervous system. As such, methods according to certain embodiments include modulating a sympathetic/parasympathetic activity ratio in the subject.

In some instances, at least a portion of the autonomic nervous system may be modulated to alter, shift or change parasympathetic activity and/or sympathetic activity from a first state to a second state, where the second state is characterized by a increase in the sympathetic activity/parasympathetic activity ratio relative to the first state. Accordingly, embodiments of the subject invention include modulating at least a portion of a subject's autonomic nervous system to increase the sympathetic activity/parasympathetic activity ratio, i.e., to increase sympathetic activity relative to parasympathetic activity (in other words to decrease parasympathetic activity relative to sympathetic activity) so as to treat a subject for a food allergy syndrome condition. Increasing the sympathetic activity/parasympathetic activity ratio may be achieved by stimulating the sympathetic system to increase activity in at least a portion of the sympathetic system, e.g., stimulating at least one sympathetic nerve fiber. Alternatively or in addition to stimulating at least one sympathetic nerve fiber to increase activity, increasing the sympathetic activity/parasympathetic activity ratio may be achieved by inhibiting activity in the parasympathetic system, e.g., inhibiting activity in at least one parasympathetic nerve fiber to achieve an increased sympathetic activity relative to parasympathetic activity. Still further, in certain embodiments the subject invention provides methods of both increasing activity in at least one sympathetic nerve fiber and inhibiting activity in at least one parasympathetic nerve fiber to achieve the desired result.

As will be described in greater detail below, while the ratio of sympathetic function/parasympathetic function may be increased according to embodiments of the subject invention to treat a subject for a condition, such as a food allergy syndrome condition, the net result may be a sympathetic bias (i.e., sympathetic dominance), or the activities of the sympathetic system and parasympathetic system may be substantially equal (i.e., neither is dominant).

By "bias", is meant that the particular "biased" component of the autonomic nervous system has a higher activity level than the other component. For example, a parasympathetic bias refers to a higher level of parasympathetic activity than sympathetic activity, and vice versa, where such bias may be systemic or localized. As such, by "vagal bias", is meant that that the particular biased component of the autonomic nervous system that has a higher activity level than the other component is the vagus nerve or a portion of the autonomic nervous system associated with the vagus nerve. Vagal bias may be characterized by one or more of vagal dominance, vagal hypersensitivity and/or sympathetic insufficiency. The net result of the subject methods to treat a condition may be higher or greater sympathetic activity relative to parasympathetic activity in at least the area of the targeted autonomic system (i.e., that portion in need of modulation), or substantially equal activity levels of sympathetic activity and parasympathetic activity.

As noted above, in certain embodiments activity in at least a portion of the autonomic nervous system is increased. For example, any portion of the sympathetic system, e.g., one or more nerve fibers, may be pharmacologically, energetically, and/or behaviorally stimulated to increase sympathetic activity to provide the desired ratio of parasympathetic/sympathetic activity. In other words, activity in at least a portion of the sympathetic nervous system may be increased pharmacologically, energetically, and/or behaviorally such that at least a portion of the sympathetic nervous system may be "up-regulated".

In certain embodiments, increasing activity in, or up-regulating, at least a part of the sympathetic system may be desired in instances where, prior to the application of autonomic nervous system-modulating energy and/or behavioral modulation and/or the administration of an effective amount of at least one pharmacological agent, parasympathetic activity is higher than desired, e.g., higher than sympathetic activity (e.g., there exists a relative parasympathetic bias) and as such the subject methods may be employed to increase sympathetic activity to a level above or rather to a level that is greater than parasympathetic activity or may be employed to modulate the differential between the parasympathetic-sympathetic systems such that the result of increasing sympathetic activity may be a sympathetic bias, parasympathetic bias or may be an equalization of the two systems (i.e., the activities of the two systems are approximately equal-including equal), but the difference between the parasympathetic-sympathetic systems may be modulated, e.g., reduced or minimized or increased in certain embodiments. Accordingly, the subject methods may be employed to increase sympathetic activity above that of parasympathetic activity and/or may be employed to modulate (increase or decrease) the differential between the two systems, but in certain embodiments may be employed to decrease the parasympathetic activity/sympathetic activity ratio.

In certain embodiments, a parasympathetic bias may be the normal state, but the ratio of the two systems may be abnormal or otherwise contributing to a condition. Increasing sympathetic bias may also be desired in instances where, prior to the application of autonomic nervous system-modulating the administration of an effective amount of at least one pharmacological agent and/or energy modulation and/or behavioral modulation, sympathetic activity is higher than the parasympathetic activity, but the differential between the two needs to be modulated such as increased further, e.g., the sympathetic activity is normal or above normal (i.e., abnormally high) and/or the parasympathetic activity is normal or below normal (i.e., abnormally low) or above normal (i.e., abnormally low).

For example, such instances may occur where a subject has normal or above normal sympathetic function, but also has elevated parasympathetic function. Other instances may include below normal sympathetic function, but normal or elevated parasympathetic function, etc. It may also be desirable to increase sympathetic function in instances where the respective activities of the two system are analogous or approximately equal, including equal, prior to increasing activity in the sympathetic system, but the level of one or both is abnormally high or abnormally low. The above-described examples of instances where increasing sympathetic activity may be desired is exemplary only and is in no way intended to limit the scope of the invention and other instances where increasing sympathetic activity may be desired will be apparent to those of skill in the art.

As noted above, in certain embodiments activity in at least a portion of the parasympathetic system may be inhibited to modulate at least a portion of the autonomic nervous system. For example, activity in any portion of the parasympathetic nervous system may be inhibited, e.g., to provide the desired ratio of parasympathetic/sympathetic activity, e.g., activity in one or more parasympathetic nerve fibers may be inhibited. By "inhibited" is meant to include disruption, down-regulating, dampening and partial and complete blockage of nerve impulses in a particular area of the autonomic nervous system.

Inhibiting or "down-regulating" activity in at least a part of the autonomic nervous system, e.g., in at least a portion of the parasympathetic system, may be desired in instances where, prior to the inhibition of activity in, e.g., at least one parasympathetic nerve fiber, the parasympathetic activity is higher than desired. For example, parasympathetic activity may be higher than the sympathetic activity (i.e., there exists a parasympathetic bias) or parasympathetic activity may be less than or approximately equal to, including equal, to sympathetic activity, and the subject methods may be employed to modulate the differential between the parasympathetic-sympathetic systems such that the net result of decreasing sympathetic activity may be a sympathetic bias, parasympathetic bias or may be an equalization of the two systems (i.e., the activities of the two systems are approximately equal-including equal), but the difference between the parasympathetic-sympathetic systems may be modulated, e.g., increased or reduced in certain embodiments. Accordingly, the subject methods may be employed to decrease parasympathetic activity below that of sympathetic activity and/or may be employed to modulate (decrease or increase) the differential between the two systems, where in certain embodiments may be employed to decrease the ratio of parasympathetic activity to sympathetic activity.

For example, decreasing activity in at least a portion of the parasympathetic system may be employed where there is a normal or an abnormally low sympathetic function and/or abnormally high parasympathetic function. Such may also be desired in instances where, prior to decreasing parasympathetic function in, e.g., at least one parasympathetic nerve fiber, sympathetic activity is higher than the parasympathetic activity, but the differential between the two needs to be increased further. For example, such instances may occur where a subject has normal or above normal (i.e., abnormally high) parasympathetic function, but also has elevated sympathetic function (i.e., abnormally high), e.g., a relative bias towards sympathetic function may be present. Other instances include normal or below normal (i.e., abnormally low) parasympathetic activity and/or normal or above normal (i.e., abnormally high) sympathetic activity. The above-described examples of instances where decreasing parasympathetic activity may be desired is exemplary only and is in no way intended to limit the scope of the invention and other instances where decreasing parasympathetic activity to provide an increase in the parasympathetic activity/sympathetic activity ratio may be desired will be apparent to those of skill in the art.

One way of inhibiting activity in at least a portion of the autonomic nervous system is by the application of a nerve block. Application of a nerve block at least partially prevents nerve transmission across the location of the block. A nerve block can be administered to modulate autonomic function using methods and devices described herein including pharmacological, energetic and/or behavioral means.

In some embodiments, a nerve block is applied to at least a portion of the vagus nerve and is called a "vagal block". Where a vagal block is applied, autonomic function in a portion of the autonomic nervous system associated with the vagus nerve can be modulated using the vagal block. In some embodiments, a nerve block is removable. In embodiments in which a nerve block is removable, removal of the nerve block restores normal or pre-existing nerve activity at the location of the block.

As the subject methods include modulating at least a portion of a subject's autonomic nervous system, the modulation may be systemic or regional (i.e., localized). In other words, the entire autonomic nervous system may be modulated (e.g., the entire sympathetic nervous system and/or parasympathetic nervous system may be modulated) or only a portion of the autonomic nervous system may be modulated (e.g., only a portion of the sympathetic nervous system and/or parasympathetic nervous system may be modulated). Localization may be with respect to a particular area, organ or even to a particular nerve fiber. For example, localization may be with respect to innervations of one or more organs.

As noted above, in certain embodiments activity in at least a portion of the autonomic nervous system may be increased and activity in at least a portion of the autonomic nervous system may be decreased. For example, in certain embodiments activity in at least a portion of the sympathetic system may be increased and activity in at least a portion of the parasympathetic system may be inhibited, e.g., to decrease the parasympathetic activity/sympathetic activity ratio. As described above, any portion of the parasympathetic and/or sympathetic nervous systems may be modulated to increase activity and activity in any portion of the sympathetic and/or parasympathetic nervous system may be inhibited to provide the desired ratio of parasympathetic activity to sympathetic activity. Such a protocol may be employed, e.g., in instances where sympathetic function is normal or abnormally low and/or parasympathetic function is normal or abnormally high where normal is determined by the typical or average autonomic nervous system functions for a healthy subject, e.g., a healthy human subject ranging in age from about 20 years old to about 25 years old.

Embodiments wherein activity in at least a portion of the autonomic nervous system may be increased and activity in at least a portion of the autonomic nervous system may be decreased may be employed to alter the dominance and/or may be employed to modulate the differential between the two systems. For example, prior to modulating the autonomic system according to the subject invention, the activity in the parasympathetic system may be higher than activity in the sympathetic system and the subject methods may be employed to increase the sympathetic activity to a level that is greater than the parasympathetic activity and/or may be employed to alter the differential or difference in activity levels of the two systems such as decreasing the difference in activity levels or increasing the difference in activity levels.

Increasing activity in at least a portion of the autonomic nervous system, e.g., increasing activity in at least a portion of the sympathetic system, and decreasing activity in at least a portion of the autonomic nervous system, e.g., decreasing activity in at least a portion of the parasympathetic system, may be performed simultaneously or sequentially such that at least a portion of the autonomic nervous system, e.g., at least a portion of the sympathetic nervous system, may be modulated to increase activity therein prior or subsequent to inhibiting activity in at least a portion of the autonomic nervous system e.g., at least a portion of the parasympathetic nervous system, such as by energetic, behavioral and/or pharmacological means.

Regardless of whether increasing activity in at least a portion of the autonomic nervous system, e.g., in at least a portion of the sympathetic system, and decreasing activity in at least a portion of the autonomic nervous system, e.g., in at least a portion of the parasympathetic system, is performed simultaneously or sequentially, the parameters for increasing activity in at least a portion of autonomic nervous system and decreasing activity in at least a portion of the autonomic nervous system may be analogous to that described above.

Modulation of the autonomic nervous system may be accomplished using any suitable method, including employing electrical, thermal, vibrational, magnetic, acoustic, baropressure, optical (e.g., light), or other sources of energy to modulate autonomic balance, where in some representative embodiments modulation is achieved via pharmacological modulation and/or energy modulation and/or behavioral modulation in a manner that is effective to treat a subject for a food allergy syndrome condition. In some embodiments, autonomic nervous system modulation may be accomplished using pharmacological modulation. In some embodiments, autonomic nervous system modulation may be accomplished using energy modulation. In some embodiments, autonomic nervous system modulation may be accomplished using behavioral modulation.

Certain embodiments include pharmacologically or energetically (e.g., electrically) or behaviorally modulating at least a portion of a subject's autonomic nervous system, e.g., that portion associated with the respiratory, digestive, integumentary or cardiovascular systems, e.g., that directly or indirectly modulates the autonomic activity of the respiratory, digestive, integumentary or cardiovascular systems, e.g., by decreasing parasympathetic activity and/or increasing sympathetic activity in at least a portion of the subject's autonomic nervous system. In certain embodiments, modulation may include increasing the sympathetic activity/parasympathetic activity ratio in at least a portion of the subject's autonomic nervous system. In certain embodiments, multiple types of modulation may be employed, including e.g., where both energetic (e.g., electrical) and pharmacological modulation may be employed, where both behavioral and energetic modulation are employed, where both behavioral and pharmacological modulation are employed, where energetic, pharmacological and behavioral modulation are employed.

Pharmacologic Modulation

As noted above, certain embodiments of the subject invention may include treating a subject for a food allergy syndrome condition by pharmacologically modulating at least a portion of the subject's autonomic nervous system. By "pharmacologically modulating at least a portion of a subject's autonomic nervous system" is meant altering or changing at least a portion of an autonomic nervous system by pharmacological means to provide a change, alteration or shift in at least one component or aspect of the autonomic nervous system. In embodiments in which pharmacological agent is administered, any suitable protocol may be used, where certain protocols include using an pharmacological agent administering device to deliver a suitable amount of pharmacological agent to a subject. Methods and corresponding devices and systems for applying at least one pharmacological agent to a subject and which may be adapted for use in the subject invention are described, e.g., in U.S. Pat. Nos. 7,363,076; 7,149,574, U.S. patent application Ser. Nos. 10/661,368; 10/748,976; 10/871,366; 10/846,486; 10/917,270; 10/962,190; 11/060,643 11/251,629; 11/238,108; 11/592,027; 60/654,139; and 60/702,776; the disclosures of which are herein incorporated by reference.

Any convenient pharmacological agent may be employed. Pro-sympathetic agents of interest include, but are not limited to: beta agonists, e.g., dobutamine, metaproterenol, terbutaline, ritodrine, albuterol; alpha agonists, e.g., selective alpha 1-adrenergic blocking agents such as phenylephrine, metaraminol, methoxamine; prednisone and steroids, (e.g., available under the brand names CORATN, DELTASONE, LIQUID PRED, MEDICORTEN, ORASONE, PANASOL-S, PREDNICEN-M, PREDNISONE INTENSOL); indirect agents that include norepinephrine, e.g., ephedrine, ampthetamines, phenylpropanolamines, cyclopentamines, tuaminoheptanes, naphazolines, tetrahydrozolines; epinephrine; norepinephrine; acetylcholine; sodium; calcium; angiotensin I; angiotensin II; angiotensin converting enzyme I ("ACE I"); angiotensin converting enzyme II ("ACE II"); aldosterone; potassium channel blockers and magnesium channel blockers, e.g., valproate (sodium valproate, valproic acid), lithium; cocaine; amphetamines; terbutaline; dopamine; doputamine; antidiuretic hormone ("ADH") (also known as vasopressin); oxytocin (including PITOCINE); THC cannabinoids; smelling salts (including e.g., ammonia compositions (e.g., dilute ammonia dissolved in water and ethanol), ammonium carbonate compositions (e.g., ammonium carbonate with perfume and/or other solvent), and the like); and combinations thereof.

In some instances, pharmacological delivery may be achieved by a device that is reversibly attached, i.e., placed in contact with a user in such a manner as the device is in sufficient contact for pharmacological delivery and may also be readily removed and/or reattached as desired. Reversibly attached devices include but are not limited to "wearable" devices. In some instances, a pharmacological delivery device may not be easily removed, including e.g., where such a device is implanted, including through invasive surgical or minimally invasive non-surgical means.

As non-limiting example of a wearable device pharmacological delivery, pharmacological delivery may be achieved by a patch with microneedles configured with one or more pharmacological delivery components (e.g., needles). In some instances, the device may include an array of microneedles that, when the subject is wearing the patch, pierce the skin of the subject to become sufficiently connected to the subject to perform the administration of the pharmacological agent, e.g., according to an open-loop or closed-loop modulation protocol. In some instances, the patch may further include a sensor for receiving an input from the subject. In some instances, one or more needles (including e.g., microneedles) may serve as both the pharmacological delivery component and the sensor.

Energetic Modulation

In certain embodiments, to accomplish the modulation of at least a portion of a subject's autonomic nervous system energy-application (energetic modulation) may be applied to at least a portion of a subject's autonomic nervous system, where such energy may be excitatory or inhibitory and in certain embodiments may include both excitatory and inhibitory stimulation. By "energetically modulating at least a portion of a subject's autonomic nervous system" is meant altering or changing at least a portion of an autonomic nervous system by energetic means to provide a change, alteration or shift in at least one component or aspect of the autonomic nervous system. Embodiments of the subject methods may also, in addition to energy application, include administering at least one pharmacological agent (pharmacological modulation) and/or at least one behavioral modulation to said subject to modulate at least a portion of a subject's autonomic nervous system.

By "energetic modulation" is meant modulating at least a portion of a subject's autonomic nervous system by applying an effective amount of energy to the subject. Various types of energy may be applied in energetic modulation including but not limited to e.g., electrical energy, vibrational energy (including e.g., ultrasonic energy and infrasonic energy), frequency specific modulation (including e.g., radio frequency specific modulation), light energy, and the like.

In certain embodiments, to accomplish the modulation of at least a portion of a subject's autonomic nervous system, electrical energy (electrical modulation) may be applied to at least a portion of a subject's autonomic nervous system, where such electrical energy may be excitatory or inhibitory and in certain embodiments may include both excitatory and inhibitory stimulation. By "electrically modulating at least a portion of a subject's autonomic nervous system" is meant altering or changing at least a portion of an autonomic nervous system by electrical means to provide a change, alteration or shift in at least one component or aspect of the autonomic nervous system. Embodiments of the subject methods may also, in addition to electrical energy, include administering at least one pharmacological agent (pharmacological modulation) and/or at least one behavioral modulation to said subject to modulate at least a portion of a subject's autonomic nervous system. In some instances, one or more other forms of energy modulation may be applied in conjunction with electrical modulation.

Useful types of electrical energy stimulation that may be employed include invasive and non-invasive techniques including direct electrical nerve stimulation methods and indirect electrical stimulation methods (including e.g., transcutaneous electrical nerve stimulation (TENS), interferential current (IFC) electrical stimulation, and the like.

Direct electrical nerve stimulation generally involves invasive methods involving the placement of one or more electrodes on, or within sufficient proximity of, a nerve to directly stimulate the nerve with an electrical current. In some instances, two electrodes may be placed on a nerve such that, when current flows between the electrodes, the nerve is affected. Direct simulation may be applied to essentially any nerve, including afferent and efferent nerves as well as nerves of the sympathetic system and parasympathetic system.

Direct electrical nerve stimulation may also include minimally invasive techniques. Such minimally invasive techniques include non-surgical implantation of one or more electrodes on, or within sufficient proximity of, a nerve to directly stimulate the nerve with an electrical current. Non-surgical methods of electrode placement may include, but are not limited to e.g., where the electrode(s) is placed using a needle inserted into the target site of the subject. Minimally invasive devices may, in some instances, include a wireless controller that is operably, but wirelessly, connected to the one or more implanted electrodes. Useful wireless controllers include e.g., an externally worn transmitter (also referred to as a wearable antenna assembly). Stimulation may be facilitated by a power source such as a battery, including e.g., where the power source is external to the subject, e.g., worn externally by the subject, and in wireless communication with the implanted electrode(s). In some instances, a receiver may be implanted into the subject operably connected to the electrode(s) and in wireless communication with a controller and/or power source, including e.g., where the controller and power source are integrated into a single component.

Non-limiting examples of minimally invasive devices, systems and components thereof that may be adapted for use in the methods, devices and systems of the present disclosure include those marketed by Stimwave LLC and described in U.S. Patent Application Pub. Nos. 20130079849; 20140058480 and 20140058481; the disclosures of which are incorporated herein by reference in their entirety.

Neurons and ganglia of the parasympathetic nervous system emerge from the brainstem as part of the Cranial nerves III, VII, IX and X (vagus nerve) and also from the sacral region of the spinal cord via Sacral nerves 2, 3 and 4. The sympathetic system includes sympathetic general visceral efferent neurons including those preganglionic cells with bodies in the lateral grey column from T1 to L2/3 which synapse with postganglionic neurons of the paravertebral ganglia and prevertebral ganglia as well as chromaffin cells of the adrenal medulla.

Branches of the autonomic nervous system that may be stimulated include parasympathetic nerve and ganglia such as, but not limited to one or more of the vagus nerve, cranial nerve III, cranial nerve VII, cranial nerve IX, sphenopalatine ganglion, ciliary ganglion, submandibular ganglion, otic ganglion, cardiac and pulmonary plexus, celiac plexus, hypogastric plexus and pelvic nerves and/or sympathetic nerve and ganglia such as, but not limited to one or more of cervical sympathetic ganglia, spinal nerves (dorsal and ventral rami), postganglionic fibers to spinal nerves (innervating skin, blood vessels, sweat glands, erector pili muscle, adipose tissue), sympathetic chain ganglia, coccygeal ganglia, cardiac and pulmonary plexus, greater splanchnic nerve, lesser splanchnic nerve, inferior mesenteric ganglion, celiac ganglion, superior mesenteric ganglion and lumber splanchnic nerves.

Indirect electrical stimulation techniques generally involve the placement of one or more electrodes externally, e.g., on the skin, over an area of a subject sufficient to stimulate one or more targeted nerves of the subject. In some instances, indirect electrical stimulation may involve two externally placed electrodes positioned such that one or more targeted nerves is between, or essentially between, the electrodes such that, when current follows between the electrodes, the targeted nerve is affected. Areas where electrodes may be placed in indirect methods of stimulation may vary and may include but are not necessarily limited to e.g., cutaneous areas, mucosal areas, cranial areas, and the like. As such, in some instances indirect simulation may be transcutaneous, transmucosal, transcranial, and the like.

In some embodiments, to accomplish the modulation of at least a portion of a subject's autonomic nervous system, transcutaneous electrical nerve stimulation (TENS) energy may be applied to at least a portion of a subject's autonomic nervous system, where such TENS energy may be excitatory or inhibitory and in certain embodiments may include both excitatory and inhibitory stimulation. By "modulating at least a portion of a subject's autonomic nervous system via TENS" is meant altering or changing at least a portion of an autonomic nervous system by TENS means to provide a change, alteration or shift in at least one component or aspect of the autonomic nervous system. Embodiments of the subject methods may also, in addition to TENS energy, include administering at least one pharmacological agent (pharmacological modulation) and/or at least one behavioral modulation to said subject to modulate at least a portion of a subject's autonomic nervous system. In some instances, one or more other forms of energy modulation may be applied in conjunction with TENS modulation.

A number of different methods and corresponding devices and systems for applying TENS energy to a subject and which may be adapted for use in the subject invention are described, e.g., in U.S. Pat. Nos. 7,200,443 and 8,428,738; as well as U.S. Patent Publication Nos. 2016/0310315 and 2018/0117017; the disclosures of which are herein incorporated by reference. Examples of a commercially available TENS units, which may be adapted for use in the methods described herein, include but are not necessarily limited to the TENS 7000 device (Roscoe Medical, Strongsville, Ohio), and the like. Methods of employing TENS stimulation that may be adapted for use in the herein described methods include TENS stimulation of the sympathetic celiac ganglia, TENS stimulation of the central nervous system, TENS stimulation of the trigeminal nerve, and TENS stimulation of the vagus nerve as described in U.S. Pat. Nos. 7,200,443 and 8,428,738 and U.S. Patent Publication Nos. 2016/0310315 and 2018/0117017, respectively, the disclosures of which are incorporated herein by reference in their entireties.

In certain embodiments, to accomplish the modulation of at least a portion of a subject's autonomic nervous system, vibrational energy (vibrational modulation) may be applied to at least a portion of a subject's autonomic nervous system, where such vibrational energy may be excitatory or inhibitory and in certain embodiments may include both excitatory and inhibitory stimulation. By "vibrationally modulating at least a portion of a subject's autonomic nervous system" is meant altering or changing at least a portion of an autonomic nervous system by vibrational means to provide a change, alteration or shift in at least one component or aspect of the autonomic nervous system. Embodiments of the subject methods may also, in addition to vibrational energy, include administering at least one pharmacological agent (pharmacological modulation) and/or at least one behavioral modulation to said subject to modulate at least a portion of a subject's autonomic nervous system. In some instances, one or more other forms of energy modulation may be applied in conjunction with vibrational modulation.

Useful types of vibrational energy that may be employed include but are not limited to e.g., ultrasonic, infrasonic, and the like.

In certain embodiments, to accomplish the modulation of at least a portion of a subject's autonomic nervous system, ultrasonic energy may be applied to at least a portion of a subject's autonomic nervous system, where such ultrasonic energy may be excitatory or inhibitory and in certain embodiments may include both excitatory and inhibitory stimulation. By "ultrasonically modulating at least a portion of a subject's autonomic nervous system" is meant altering or changing at least a portion of an autonomic nervous system by ultrasonic means to provide a change, alteration or shift in at least one component or aspect of the autonomic nervous system. Embodiments of the subject methods may also, in addition to ultrasonic energy, include administering at least one pharmacological agent (pharmacological modulation) and/or at least one behavioral modulation to said subject to modulate at least a portion of a subject's autonomic nervous system. In some instances, one or more other forms of energy modulation may be applied in conjunction with ultrasonic modulation.

A number of different methods and corresponding devices and systems for applying ultrasonic energy to a subject and which may be adapted for use in the subject invention are described, e.g., in U.S. Pat. Nos. 5,413,550, 7,283,861, and 8,715,209; as well as U.S. Patent Publication Nos. 2011/0112394, 2011/0130615, 2011/0178442, 2011/0208094, 2017/0080255, 2012/028350, 2011/0190668, 2014/0343463, and 2007/0203432; the disclosures of which are herein incorporated by reference. For example, methods of applying ultrasonic energy to a subject that may be adapted for use in the herein described methods include e.g., non-invasive deep brain and superficial neuromodulation with ultrasound of 0.3 MHz to 0.8 MHz as described in US 2011/0112394, 2011/0130615, 2011/0178442, 2011/0208094, and US 2012/0283502; ultrasound of 0.3 MHz to 0.8 MHz used to modulate the sphenopalatine ganglion and associated structures as described in U.S. Patent Publication Nos. 2011/0190668 and 2014/034363; ultrasound of 0.1 MHz to 1 MHz used to stimulate brain tissue as described in U.S. Patent Publication No. 2017/0080255; and ultrasound used to target sympathetic nerves as described in U.S. Pat. No. 8,715,209; the disclosures of which are incorporated herein by reference in their entireties. In some instances, the use of focused ultrasound pulses, e.g., as described in U.S. Pat. No. 7,283,861, may be adapted for use in the herein described methods.

In certain embodiments, to accomplish the modulation of at least a portion of a subject's autonomic nervous system, infrasonic energy may be applied to at least a portion of a subject's autonomic nervous system, where such infrasonic energy may be excitatory or inhibitory and in certain embodiments may include both excitatory and inhibitory stimulation. By "infrasonically modulating at least a portion of a subject's autonomic nervous system" is meant altering or changing at least a portion of an autonomic nervous system by infrasonic means to provide a change, alteration or shift in at least one component or aspect of the autonomic nervous system. Embodiments of the subject methods may also, in addition to infrasonic energy, include administering at least one pharmacological agent (pharmacological modulation) and/or at least one behavioral modulation to said subject to modulate at least a portion of a subject's autonomic nervous system. In some instances, one or more other forms of energy modulation may be applied in conjunction with infrasonic modulation.

A number of different methods and corresponding devices and systems for applying infrasonic energy to a subject and which may be adapted for use in the subject invention are described, e.g., in U.S. Pat. Nos. 8,517,911, 9,457,166, 9,480,812; as well as U.S. Patent Publication Nos. 2007/0203432, and 2016/0262974; the disclosures of which are herein incorporated by reference. For example, methods of applying infrasonic energy to a subject that may be adapted for use in the herein described methods include e.g., sound vibration frequencies transmitted to the spinal cord as described in U.S. Pat. No. 9,480,812; acoustic vibrations with frequencies as low as 10 Hz as described in U.S. Patent Publication No. 2007/0203432; and infrasound with binaural frequencies less than 40 Hz as described in U.S. Patent Publication No. 2016/0262974; the disclosures of which are incorporated herein by reference in their entireties.

In some instances where vibrational energy is employed, including e.g., infrasonic and/or ultrasonic, the applied vibrational energy may exclude vibrational energy within ranges audible to humans. For example, in some instances, the applied vibrational energy may exclude vibrations from about 20 Hz to about 20,000 Hz. In some instances, vibrational energy employed may include frequencies within the range of human hearing, including e.g., where a range of infrasonic frequencies are used that overlaps with the range audible to humans, where a range of ultrasonic frequencies are used that overlaps with the range audible to humans.

In certain embodiments, to accomplish the modulation of at least a portion of a subject's autonomic nervous system, frequency specific energy modulation (frequency specific modulation) may be applied to at least a portion of a subject's autonomic nervous system, where such frequency specific energy may be excitatory or inhibitory and in certain embodiments may include both excitatory and inhibitory stimulation. By "frequency specifically modulating at least a portion of a subject's autonomic nervous system" is meant altering or changing at least a portion of an autonomic nervous system by frequency specific means to provide a change, alteration or shift in at least one component or aspect of the autonomic nervous system. Embodiments of the subject methods may also, in addition to frequency specific energy, include administering at least one pharmacological agent (pharmacological modulation) and/or at least one behavioral modulation to said subject to modulate at least a portion of a subject's autonomic nervous system. In some instances, one or more other forms of energy modulation may be applied in conjunction with frequency specific modulation.

A number of different methods and corresponding devices and systems for applying frequency-specific modulation energy to a subject and which may be adapted for use in the subject invention are described, e.g., in U.S. Pat. Nos. 9,808,641, 10,010,713, 10,155,114; as well as U.S. Patent Publication No. 2019/0001135; the disclosures of which are herein incorporated by reference. For example, methods of applying frequency-specific modulation energy to a subject that may be adapted for use in the herein described methods include e.g., method involving the excitation of frequency-specific nerve populations as described in U.S. Pat. No. 10,010,713; noise stimulation used to disrupt ongoing connectivity frequency-specific transmission between different areas of the nervous system as described in U.S. Pat. No. 10,155,114; and frequency-specific electrodes and specific frequency intervals used to non-invasively stimulate nerve tissue as described in U.S. Pat. No. 9,808,641; and varied frequencies of electrical stimulation based on frequency specific results (e.g. between 2 Hz and 30 Hz) as described in U.S. Patent Publication No. 2019/0001135; the disclosures of which are incorporated herein by reference in their entireties.

A number of different methods and corresponding devices and systems and parameters for applying frequency-specific modulation to a subject and which may be adapted for use in the subject invention are described, e.g., in Dakin et al., Frequency-Specific Modulation of Vestibular-Evoked Sway Responses in Humans, J. of Neurophysiol., 2010, 103(2): 1048-1056; Chanes et al., Causal Frequency-Specific Contributions of Frontal Spatiotemporal Patterns Induced by Non-Invasive Neurostimulation to Human Visual Performance, Journal of Neuroscience 2013, 33(11):5000-5005; and Feurra et al., Frequency specific modulation of human somatosensory cortex, Front. Psychol., 2011; the disclosures of which are herein incorporated by reference. Useful devices, and components and parameters thereof, for frequency specific modulation, that may be adapted for use in the herein described methods, also include those employing radio frequency (RF) modulation, such as but not limited to e.g., the Abbott NT2000iX™ RF Generator and Simplicity™ probe.

In certain embodiments, to accomplish the modulation of at least a portion of a subject's autonomic nervous system, light energy may be applied to at least a portion of a subject, including e.g., at least a portion of a subject's autonomic nervous system, where such light energy may be excitatory or inhibitory and in certain embodiments may include both excitatory and inhibitory stimulation. By "modulating at least a portion of a subject's autonomic nervous system using light energy" is meant altering or changing at least a portion of an autonomic nervous system by applying light to the subject to provide a change, alteration or shift in at least one component or aspect of the autonomic nervous system. Embodiments of the subject methods may also, in addition to light energy, include administering at least one pharmacological agent (pharmacological modulation) and/or at least one behavioral modulation to said subject to modulate at least a portion of a subject's autonomic nervous system. In some instances, one or more other forms of energy modulation may be applied in conjunction with light modulation.

Light energy may be applied to a subject in a variety of ways, including where the light is applied through visual and/or non-visual tracts. For example, in some instances, light may be applied to modulate a subject's autonomic nervous system through the optic nerve, e.g., by application of the light energy directly or indirectly to a visual field of a subject such that the light energy is perceived through the eyes of the subject. In some instances, light energy may be applied in a manner effective to influence activity in the visual cortex through a visual tract. In some instances, light energy may be applied in a manner effective to influence activity through a non-visual tract. e.g., by influencing activity in the retinohypothalamic tract.

By "light energy" is generally meant electromagnetic radiation in the visible and/or near-visible ranges (e.g., ultraviolet and/or infrared). Light energy may be mono- or polychromatic. Accordingly, various wavelengths of light energy may be employed in the subject methods, including where a range of wavelengths or a single wavelength or multiple single wavelengths are applied to a subject.

The term "range of wavelengths" as used herein generally refers polychromatic light that includes to a collection of adjacent wavelengths that may wholly or partially cover a particular band of a spectrum or may span one or more spectral bands. Bands of the spectrum include but are not necessarily limited to the visible band (about 380 nm to about 750 nm), the infrared band (about 750 nm to about 1 mm), the red band (about 620 nm to about 750 nm), the orange band (about 590 nm to about 620 nm), the yellow band (about 570 nm to about 590 nm), the green band (about 495 nm to about 570 nm), the blue band (about 450 nm to about 495 nm), the violet band (about 380 nm to about 450 nm), and the ultraviolet band (about 10 nm to about 380 nm). Infrared bands may be subdivided including e.g., where -divisions of infrared light include but are not limited to e.g., near-infrared (about 750 nm to about 1.4 µm), short-wavelength infrared (about 1.4 µm to about 3 µm), mid-wavelength infrared (about 3 µm to about 8 µm), long-wavelength infrared (about 8 µm to about 15 µm), and far infrared (about 15 µm to about 1 mm). Accordingly, in some instances, a range of wavelengths may be defined according to the band or bands within the range, including e.g., those bands described above. Application of light energy may, in some instances, include or exclude one or more bands of light.

In some instances, a range of wavelengths may be defined numerically including e.g., wavelengths ranging from 10 nm to 50 nm, 10 nm to 100 nm, 10 nm, to 200 nm, 100 nm to 200 nm, 200 nm to 300 nm, 300 nm to 400 nm, 400 nm to 500 nm, 500 nm to 600 nm, 600 nm to 700 nm, 700 nm to 800 nm, 800 nm, to 900 nm, 900 nm to 1 mm, etc. The size of a range of wavelengths (i.e., bandwidth) will vary and may range from 5 nm or less to 500 nm or more, including but not limited to e.g., a bandwidth of 5 nm, of 10 nm, of 15 nm, of 20 nm, of 25 nm, of 30 nm, of 40 nm, of 50 nm, of 60 nm, of 70 nm, of 80 nm, of 90 nm, of 100 nm, of 150 nm, of 200 nm, of 250 nm, of 300 nm, of 400 nm, of 500 nm, etc. Application of light energy may, in some instances, include or exclude one or more ranges of wavelengths, including ranges of wavelengths of various bandwidths.

A range of wavelengths of light (polychromatic light) may be applied to a subject using a variety of light emitters, including but not limited to e.g., a blub or lamp (e.g., arc lamp, ultraviolet lamp, incandescent lamp, gas-discharge lamp, infrared lamp, etc.), a light emitting diode (LED) (e.g., visible spectrum LED (e.g., red, orange, yellow, green, blue, and violet LEDs), ultraviolet LED, infrared LED, etc.), or the like. Employed light sources emit artificial light. One or more desired bands of light or a range of wavelengths may be applied using a light emitter, such as a broad-spectrum light emitter, in conjunction with one or more optical filters, such as e.g., a long-pass filter, a short-pass filter, a band-pass filter, or a combination thereof.

In some instances, a single wavelength (monochromatic light), or multiple single wavelengths (multiple monochromatic lights), may be applied to a subject. Essentially any single wavelength, or collection of single wavelengths, of light (including visible, ultraviolet, or infrared wavelengths) may be employed as desired. In some instances, a laser or a laser diode (LD) may be employed to administer light of a particular wavelength or collection of particular wavelengths, including but not limited to e.g., helium-neon lasers, argon lasers, krypton lasers, xenon lasers, excimer lasers, dye lasers, ruby lasers, neodymium-doped yttrium aluminum garnet lasers, erbium-doped yttrium aluminium garnet lasers, holmium YAG lasers, chromium doped chrysoberyl (alexandrite) lasers, and LDs of various specific wavelengths.

Light energy may be applied directly to a subject, e.g., by orienting a light application device such that the light emitted from the device is directed to and/or on the subject. Application of light includes, but is not limited to e.g., application of light to the eye(s) of the subject (including where the application to the eye(s) serves to apply the light energy directly to the central nervous system of the subject, e.g., via the optic nerve, including the visual cortex and/or the retinohypothalamic tract). Direct application may also include application of light to one or more areas of the subject other than the eyes, such as but not limited to e.g., the skin or head of a subject, such as e.g., by placing a light emitter on or within sufficient proximity of the skin or head to apply the light to the desired target. Accordingly, direct application includes non-invasive application of the light energy; however, invasive means may also be employed. For example, direct application may also include applying light energy directly to an internal structure (such as a nerve) of the subject, e.g., as accessed by surgical (including orthoscopic) manipulation of the subject.

Light energy applied to a subject may be continuous or discontinuous, e.g., pulsed. Continuous application of light energy may include applying light energy to a subject in a single application for a defined period of time, including e.g., minutes, hours, days, weeks, or months. Discontinuous application of light energy may include multiple, including e.g., multiple rapid, applications of light energy to a subject with intervening non-application periods in a single treatment. Pulsed application of light energy may include pulses and non-application periods of various lengths, including but not limited to lengths ranging from 1 microsecond or less to multiple seconds, including, e.g., 1 µs to 10 s, 10 µs to 10 s, 10 µs to 1 s, 100 µs to 10 s, 100 µs to 1 s, etc. Pulses of light energy may be administered at various frequencies ranging from 0.5 Hz or less to 100 Hz or more, including but not limited to e.g., 0.5 Hz to 100 Hz, 0.5 Hz to 10 Hz, 1 Hz to 100 Hz, 1 Hz to 10 Hz, 1 Hz to 5 Hz, 5 Hz to 10 Hz, 5 Hz to 50 Hz, 5 Hz to 100 Hz, 10 Hz to 100 Hz, etc. In some instances, the application of light energy to a subject may employ parameters similar to electrical stimulation, including but not limited to e.g., where infrared neural stimulation is applied with parameters similar to electrical neural stimulation. Non-limiting examples of useful light application parameters include e.g., pulsed stimulation having a pulse length of 10 to 1000 microseconds at 1 to 10 Hz, including e.g., 35 to 1000 µs pulses of infrared light of a wavelength between 850 nm and 2 µm at a repetition rate of 2 Hz.

A number of different methods, corresponding devices, systems and parameters for applying light energy to a subject and which may be adapted for use in the subject invention are described in, e.g., Tsai & Hamblin, J Photochem Photobiol B. (2017) 170:197-207; de Freitas & Hamblin IEEE J Sel Top Quantum Electron. (2016) 22(3): 7000417; Ross et al. Adv Mind Body Med. (2013) 27(4): 7-16; and in U.S. Pat. Nos. 950,189; 9,610,022; 9,696,804; 9,717,904; 9,782,221; 9,833,276; 9,968,541; 9,919,162; 9,993,661; 10,111,729; 10,118,049; 10,149,975; 10,155, 121; 10,183,174; 10,188,872; 10,219,944; 10,252,077; 10,252,078; and RE47,266; the disclosures of which are herein incorporated by reference.

Targeting of energy-application modulation may depend on the type of energy applied, where essentially any suitable area may be targeted for energetic modulation. Various forms of energy (e.g., electrical, vibrational, frequency specific, etc.) may be broadly applied to target significant portions of a subject's autonomic nervous system. Focused energy (e.g., focused ultrasound, focused electrical energy) and directly applied energy (e.g., electrical stimulation via implanted electrode, directly applied vibrational energy, directly applied frequency specific energy, etc.) may be employed to target a limited area, including nerve fibers, individual nerves, groups of nerves, and the like.

Any suitable area may be targeted for energetic, including electrical, modulation. Areas that may be targeted include, but are not limited to, pre- and post-ganglionic nerve fibers, as well as ganglionic structures, efferent and afferent nerve fibers, synapses, etc., and combinations thereof in certain embodiments. In certain embodiments, activity in a given nerve fiber may be modulated, including electrically modulated, in more than one area of the nerve fiber. In certain embodiments, energy, including electrical energy, is applied to modulate synaptic efficiency, e.g., to increase or decrease the sensitivity of a synapse and include modulating presynaptic neurons. In certain embodiments, energy, including electrical energy, is applied using any of the devices described below.

A number of different methods and corresponding devices and systems for applying electrical energy to a subject and which may be adapted for use in the subject invention are described, e.g., in U.S. Pat. Nos. 7,149,574; 7,711,430; and 7,363,076; as well as U.S. patent application Ser. No. 11/592,027; the disclosures of which are herein incorporated by reference.

Energy application to a subject may be performed in a variety of ways. For example, in some instances, an energy application device, or a component thereof, may be implanted into or affixed on a subject. In some embodiments, one or more energy application components of a device, such as one or more electrodes, one or more vibrational stimulators, or the like, may be surgically implanted on, or within sufficient proximity to, a targeted nerve for direct modulation by the energy application component(s) of the device. Such energy application components may be operably connected to other components of the device, such as a controller, by any convenient connection, including wired and wireless connections.

Devices employed in the subject methods may be autonomous (including wholly or partially autonomous) or user-controlled. User-controlled devices may operate in an open-loop manner. Accordingly, user-interface components of a device, e.g., a device employing implanted energy application components, may be accessible such that the user may interact with and/or activate the device to provide the desired modulation. In some instances, an implanted device, or device attached to a surface (e.g., skin, scalp, etc.) of a subject, may be autonomous such that the device need not include user-accessible components. In some instances, autonomous devices may operate in a closed-loop manner, e.g., sensing an input from the subject and administering a corresponding energy modulation based on the sensed input.

In some instances, energy application may be applied by a device that is reversibly attached, i.e., placed in contact with a user in such a manner as the device is in sufficient contact for energy application and may also be readily removed and/or reattached as desired. Reversibly attached devices include but are not limited to "wearable" devices, nonlimiting examples of which include wristbands, wristwatches, earpieces, eyewear (e.g., glasses, etc.), neck-ware and jewelry (e.g., necklaces, collars, earrings, etc.), footwear, patches, and the like.

As a non-limiting example, energy application may be applied by a wristband or wristwatch configured with one or more energy application components (e.g., electrodes, vibrational stimulators, light emitters, etc.) that, when the subject is wearing the wristband or wristwatch, are operably connected to the subject to perform the modulation, e.g., according to an open-loop or closed-loop modulation protocol. In some instances, the wristband or wristwatch may further include a sensor for receiving an input from the subject. In some instances, the energy application component and the sensor may be integrated or may be a single component useful for both purposes.

As another non-limiting example, energy application may be applied by a patch with microneedles configured with one or more energy application components (e.g., electrodes) in the form of microneedles that, when the subject is wearing the patch, pierce the skin of the subject to become operably connected to the subject to perform the modulation, e.g., according to an open-loop or closed-loop modulation protocol. In some instances, the patch may further include a sensor for receiving an input from the subject. In some instances, the microneedles may serve as both the energy application component and the sensor.

In some instances, a wearable device may include one or more components for receiving input from a wearer, including e.g., where such input detects one or more aspects of the autonomic nervous system of the subject. Input receiving components of a wearable device may be non-invasive, minimally invasive or invasive. Useful components for receiving input include user-interface components, sensors, and the like. For example, non-invasive sensors that may be employed in a wearable device may include, but are not limited to, optical sensors. Examples of non-invasive sensors, and devices employing non-invasive sensors, such as electrical (e.g., electrocardiography (ECG)) and optical (e.g., photoplethysmography (PPG)) or other biophysical (e.g., carbon dioxide levels, oxygen saturation levels, glucose levels, and the like) sensors that may be adapted for use in the methods, devices and systems described herein include those described below. Invasive and minimally invasive sensors that may be employed in the methods of the present disclosure or adapted for use in a subject wearable device may include, but are not limited to, electrodes that may be surgically or non-surgically, respectively, implanted into a subject. Examples of implantable electrodes that may be adapted for use in the herein described methods, systems, and devices include those described herein and also include those marketed by Stimwave LLC and described in U.S. Patent Application Pub. Nos. 20130079849; 20140058480 and 20140058481; the disclosures of which are incorporated herein by reference in their entirety.

In some instances where an electrical protocol is employed, the target condition is not a bronchoconstriction condition, such as asthma, e.g., as described in United States Patent Application 20120004701.

Behavioral Modulation

In certain embodiments, to accomplish the modulation of at least a portion of a subject's autonomic nervous system behavioral modulation may be applied, resulting in a modulation to at least a portion of a subject's autonomic nervous system, where such behavioral modulation may result in excitatory or inhibitory modulation to portions of the autonomic nervous system, including where, in certain embodiments, the modulation may result in both excitatory and inhibitory stimulation to portions of the autonomic nervous system. By "behaviorally modulating at least a portion of a subject's autonomic nervous system" is meant altering or changing at least a portion of an autonomic nervous system by behavioral means to provide a change, alteration or shift in at least one component or aspect of the autonomic nervous system. Embodiments of the subject methods may also, in addition to behavioral modulation, include administering at least one pharmacological agent (pharmacological modulation) and/or at least one type of energy application to said subject to modulate at least a portion of a subject's autonomic nervous system.

Behavioral protocols for modulating at least a portion a subject's autonomic nervous system will vary and may involve actions performed by a subject that induce in the subject a physiological response that results in modulation of at least a portion of the subject's autonomic nervous system.

In some embodiments, a subject behavioral protocol may include controlled breathing exercises. The typical respiratory rate in non-infant humans is within the range of 10 to 20 breaths per minute (0.16 to 0.33 Hz). Controlled breathing exercises include metered breathing where, e.g., breaths are metered at a rate above or below the typical respiratory rate. In some instances, metered breathing may include slow breathing (i.e., induced bradypnea) of a rate below 10 breaths per minute, including but not limited to e.g., less than 10 breaths per min., less than 8 breaths per min., less than 6 breaths per min., less than 4 breaths per min., including e.g., where such slow breathing includes any rate of breathing from 4 to 10 breaths per minute (0.07 to 0.16 Hz).

In some instances, metered breathing may include rapid breathing (i.e., induced tachypnea) of a rate above 20 breaths per minute, including but not limited to e.g., more than 20 breaths per min., more than 22 breaths per min., more than 24 breaths per min., more than 26 breaths per min., more than 28 breaths per min., more than 30 breaths per min., more than 32 breaths per min., more than 34 breaths per min., more than 36 breaths per min., more than 38 breaths per min., more than 40 breaths per min., including e.g., where such rapid breathing includes any rate of breathing from above 20 to 40 breaths per minute or greater (0.33 to 0.67 Hz).

In some instances, behavioral modulation may be employed to modulate a subject's carbon dioxide levels and/or oxygen saturation levels. For example, in some instances, controlled breathing may be employed to raise a subject's carbon dioxide levels or oxygen saturation levels. In some instances, controlled breathing may be employed to decrease a subject's carbon dioxide levels or oxygen saturation levels. In some instances, hyperventilation may be induced or prevented using a metered breathing exercise. Hyperventilation is abnormally increased pulmonary ventilation, resulting in a reduction of carbon dioxide tension (below normal alveolar carbon dioxide pressure), which, if prolonged, can lead to alkalosis. In some instances, hypoventilation may be induced or prevented using a metered breathing exercise. Hypoventilation is the state in which a reduced amount of air enters the alveoli in the lungs, resulting in decreased levels of oxygen and increased levels of carbon dioxide in the blood. Hypoventilation can be due to breathing that is abnormally shallow (hypopnea) or abnormally slow (bradypnea).

In some instances, behavioral modulation may include one or more mental practices, physical maneuvers and/or exposure to an environmental stimulus that trigger(s) one or more autonomic nervous system reflexes. Mental practices, physical maneuvers and environmental stimuli that trigger autonomic nervous system reflexes include but are not limited to e.g., isometric exercise (e.g., as performed during an isometric handgrip test), exposure to cold (e.g., as performed during a cold pressor test), exposure to heat (e.g., as performed during a thermoregulatory sweat test), mental arithmetic, Valsalva maneuver, head and/or body tilting (e.g., as performed during a tilt table test), neck chamber (baroreflex) application (e.g., by application of negative pressure to the neck by means of a moldable lead collar), carotid sinus message, and the like.

Useful mental practices include, e.g., meditation. As used herein, the term "meditation" generally involves continuous and profound contemplation or musing on one or more subjects or series of subjects of a deep or abstruse nature and may include methods of training a subject's attention or awareness to bring bodily processes, including mental processes, under voluntary control. As a non-limiting example, a software application (i.e., "app") may provide a guided mediation exercise that may be administered via a device, such as a personal computer, tablet computer or smartphone, that includes the app stored thereon.

In some embodiments, implementation of a behavioral modification may employ biofeedback. As used herein, "biofeedback" generally refers to the induction of a behavioral modulation based on visual, auditory or other (e.g., tactile) feedback. Relevant feedback for autonomic nervous system modulation will generally include feedback pertaining to the state of the subject's autonomic nervous system, including but not limited to e.g., sympathetic activity, parasympathetic activity, sympathetic/parasympathetic activity balance, and the like. Such feedback may be directly provided to the user, e.g., as a direct readout of the state of the subject's autonomic nervous system, or the feedback may be indirectly provided, e.g., through the integration of the feedback into one or more subsequently induced behavioral modulations.

For example, in the case of direct biofeedback, a subject's autonomic nervous system may be assessed, e.g., the sympathetic/parasympathetic balance of the subject may be determined, and the subject may be provided with a direct indication of the result of the assessment, e.g., through as a visual, auditory or other signal to the user that directly relates to, e.g., the measured level of the subject's sympathetic/parasympathetic activity ratio. Non-limiting examples of visual, auditory or other signals that may be provided to a subject as direct forms of biofeedback include: a visual numerical value representative of the measurement of the subject's autonomic nervous system (e.g., a score of the subject's sympathetic/parasympathetic activity ratio, e.g., as assessed by HRV); a visually provided color representative of the measurement of the subject's autonomic nervous system (e.g., a color along a spectrum correlating with a score of the subject's sympathetic/parasympathetic activity ratio, e.g., as assessed by HRV); an auditory tone representative of the measurement of the subject's autonomic nervous system (e.g., a tone of a particular frequency along a range of audible frequencies correlating with a score of the subject's sympathetic/parasympathetic activity ratio, e.g., as assessed by HRV); a tactile signal (e.g., a vibration) representative of the measurement of the subject's autonomic nervous system (e.g., a vibration of a particular amplitude along a range correlating with a score of the subject's sympathetic/parasympathetic activity ratio, e.g., as assessed by HRV).

In some instances, visual, auditory or other signals may be configured to correlate with reference values for the assessed measure of the subject's autonomic nervous system. In some instances, visual, auditory or other signals may be configured to correlate with a previous value for the assessed measure of the subject's autonomic nervous system. For example, the visual, auditory or other signal provided to the subject may be based on a prior measured value, including e.g., where the signal indicates an increase when the current score is improved relative to the prior score or indicates a decrease when the current score is lower relative to the prior score. In some instances, the signal may be provided in a real-time manner.

In some instances, behavioral modulation may be coupled with monitoring of the subject's autonomic nervous system, including where monitoring is performed intermittently or in real-time. For example, methods of the present disclosure may employ a device that monitors sympathetic/parasympathetic function of a subject and triggers a behavioral modulation of the subject's autonomic nervous system based on the monitoring.

Using slow breathing as a non-limiting example, without being bound by theory, it is noted that slow breathing increases vagal activity and has been shown, e.g., after extended practice, to result in a shift towards parasympathetic dominance. However, during slow breathing, sympathetic bursts are also observed and, in some instances, slow breathing drives towards sympathovagal balance, particularly related to the ability for sympathetic/parasympathetic balance to be restored in response to physical perturbations. Accordingly, the physiological effects of controlled breathing are complex.

Accordingly, in some instances, behavioral modulation, such as controlled breathing, may be coupled with monitoring to produce the desired modulation of the subject's autonomic nervous system based on the monitoring. For example, a subject may perform a controlled breathing exercise, such as rapid or slow breathing, as paced by a device that also monitors the subject's parasympathetic and sympathetic activity. The device may then, periodically or in real-time, adjust the pacing according to the monitoring. For example, the device may increase or decrease the pacing, based on the monitoring, to achieve the desired modulation of the subject's autonomic nervous system, including e.g., where the desired modulation is an increase in the sympathetic/parasympathetic activity ratio, and/or a balancing of sympathetic and parasympathetic activity.

In some instances, behavioral modulation, such as mental practices, including meditation, may be coupled with monitoring to produce the desired modulation of the subject's autonomic nervous system based on monitoring. For example, a subject may perform a mediation exercise as guided by a device that also monitors the subject's parasympathetic and sympathetic activity. The device may then, periodically or in real-time, adjust the guided mediation according to the monitoring. For example, the device may increase or decrease the rate and/or intensity of the guided meditation, based on the monitoring, to achieve the desired modulation of the subject's autonomic nervous system, including e.g., where the desired modulation is an increase in the sympathetic/parasympathetic activity ratio, and/or a balancing of sympathetic and parasympathetic activity. As a non-limiting example, a software application (i.e., "app") administered via a device, such as a personal computer, tablet computer or smartphone, may provide a guided mediation and the subject may be monitored by the device or a separate device that is operably connected to the app so as to provide for adjustment of the app based on the monitoring.

In some instances where a behavioral protocol is employed, the target condition is not a bronchoconstriction condition, such as asthma.

Combinatorial Modulation

In certain embodiments, to accomplish the modulation of at least a portion of a subject's autonomic nervous system a combination of pharmacological, energetic and/or behavioral modulation may be applied, resulting in a modulation to at least a portion of a subject's autonomic nervous system, where such combinatorial modulation may result in excitatory or inhibitory modulation to portions of the autonomic nervous system, including where, in certain embodiments, the modulation may result in both excitatory and inhibitory stimulation to portions of the autonomic nervous system. Any combination of the herein described modulations may be employed.

For example, in some instances, a combinatorial modulation that includes at least one pharmacological modulation and at least one energetic modulation may be employed. In some embodiments, a combinatorial modulation may be employed that includes administering a pro-sympathetic agent and one or more of electrical energy, vibrational energy (including e.g., ultrasonic energy and infrasonic energy), frequency specific modulation (including e.g., radio frequency specific modulation), or light energy. In some instances, a device may be employed that administers such a combinatorial modulation, including e.g., a device configured for administering at least one pharmacological agent to a subject and administering at least one of electrical energy, vibrational energy (including e.g., ultrasonic energy and infrasonic energy), frequency specific modulation (including e.g., radio frequency specific modulation), or light energy to the subject. Pharmacological and energetic combinatorial modulation may include where the pharmacological and energetic modulations are co-administered, including simultaneous and non-simultaneous co-timely administration.

In some instances, a combinatorial modulation that includes at least one pharmacological modulation and at least one behavioral modulation may be employed. In some embodiments, a combinatorial modulation may be employed that includes administering a pro-sympathetic agent and one or more of controlled breathing exercises or mental practices, physical maneuvers and/or exposure to an environmental stimulus that trigger(s) one or more autonomic nervous system reflexes. In some instances, a device may be employed that administers such a combinatorial modulation, including e.g., a device configured for administering at least one pharmacological agent to a subject and administering at least one of controlled breathing exercises or mental practices, physical maneuvers and/or exposure to an environmental stimulus that trigger(s) one or more autonomic nervous system reflexes. Pharmacological and behavioral combinatorial modulation may include where the pharmacological and behavioral modulations are co-administered, including simultaneous and non-simultaneous co-timely administration.

In some instances, a combinatorial modulation that includes at least one energetic modulation and at least one behavioral modulation may be employed. In some embodiments, a combinatorial modulation may be employed that includes administering one or more of electrical energy, vibrational energy (including e.g., ultrasonic energy and infrasonic energy), frequency specific modulation (including e.g., radio frequency specific modulation), or light energy in combination with one or more of controlled breathing exercises or mental practices, physical maneuvers and/or exposure to an environmental stimulus that trigger(s) one or more autonomic nervous system reflexes. In some instances, a device may be employed that administers such a combinatorial modulation, including e.g., a device configured for administering at least one of electrical energy, vibrational energy (including e.g., ultrasonic energy and infrasonic energy), frequency specific modulation (including e.g., radio frequency specific modulation), or light energy in combination with at least one of controlled breathing exercises or mental practices, physical maneuvers and/or exposure to an environmental stimulus that trigger(s) one or more autonomic nervous system reflexes. Energetic and behavioral combinatorial modulation may include where the energetic and behavioral modulations are co-administered, including simultaneous and non-simultaneous co-timely administration.

In some instances, a combinatorial modulation that includes at least one pharmacological modulation, at least one energetic modulation and at least one behavioral modulation may be employed. In some embodiments, a combinatorial modulation may be employed that includes: (i) administering a pro-sympathetic agent; in combination with (ii) one or more of electrical energy, vibrational energy (including e.g., ultrasonic energy and infrasonic energy), frequency specific modulation (including e.g., radio frequency specific modulation), or light energy; and in combination with (iii) one or more of controlled breathing exercises or mental practices, physical maneuvers and/or exposure to an environmental stimulus that trigger(s) one or more autonomic nervous system reflexes. In some instances, a device may be employed that administers such a combinatorial modulation, including e.g., a device configured for administering: (i) at least one pharmacological agent to a subject; (ii) at least one of electrical energy, vibrational energy (including e.g., ultrasonic energy and infrasonic energy), frequency specific modulation (including e.g., radio frequency specific modulation), or light energy; and (iii) at least one of controlled breathing exercises or mental practices, physical maneuvers and/or exposure to an environmental stimulus that trigger(s) one or more autonomic nervous system reflexes. Pharmacological, energetic and behavioral combinatorial modulation may include where the pharmacological, energetic and behavioral modulations are co-administered, including simultaneous and non-simultaneous co-timely administration.

Paradoxical Modulation

In some instances, the methods include employing a paradoxical protocol in order to obtain the desired increase is sympathetic/parasympathetic activity ratio. In these embodiments, the sympathetic/parasympathetic activity ratio is decreased initially in a manner effective to cause the subject to mount a compensatory response effective to ultimately increase the sympathetic/parasympathetic activity ratio. In certain embodiments, the magnitude of decrease in the sympathetic/parasympathetic activity ratio is two-fold or greater, e.g., 5-fold or greater.

In practicing the subject methods, the sympathetic/parasympathetic activity ratio is decreased by applying an appropriate stimulus to the subject, where the stimulus is of a nature and magnitude sufficient to achieve the desired enhancement. In certain embodiments, the applied stimulus is one of short duration, where by short duration is meant that the applied stimulus lasts for less than about 1 week, e.g., less than about 3 days, e.g., less than about 1 day, e.g., less than about 12 hours, where the duration of the applied stimulus may be even shorter. Where the stimulus is a pharmacological stimulus, the duration refers to the period in which the pharmacological agent from an administered dosage is active. Where the stimulus is an energetic stimulus (e.g., an electrical stimulus), the duration refers to the total of energy applications received by a subject over a given period, analogous to a dose of a pharmacological agent.

Following decrease of the sympathetic/parasympathetic activity ratio via an applied stimulus, as described above, the stimulus is removed, e.g., by metabolization of the pharmacological agent or cessation of application of energy, and the subject is permitted to mount a compensatory response. In this following period, no additional stimulus is administered to the subject. The duration of this period between stimulus application, which may be referred to as a "holiday" period, may vary, but in representative embodiments is 1 day or longer, such as 2 days or longer, including 5 days or longer, 10 days or longer, e.g., 15 days or longer. As such, embodiments of the methods include non-chronic (i.e., non-continuous) application of the stimulus, e.g., non-chronic administration of a pharmacologic agent.

In certain embodiments, the methods include close monitoring or supervision of the subject during and/or after application of the stimulus. This monitoring may be completely automated, or at least in part performed manually, e.g., by a health care professional. For example, a health care professional can closely watch the subject following application of the stimulus as well as during the holiday period following stimulus application, and based on this monitoring determine when a next stimulus should be applied. Monitoring also assures that the symptom enhancement is not so severe as to be ultimately damaging to the subject at an unacceptable level. Certain aspects of the monitoring may be automated. For example, following administration, the subject may enter one or more physiological parameters into an automated system, which uses the input parameters to automatically determine whether the subject is staying within a predetermined set of physiological parameters, or whether intervention is necessary. In certain embodiments, the automated monitoring system may also be integrated with a stimulus application device, such that the system, based on monitored parameters, determines when next to administer a stimulus, the duration of the next stimulus, etc. As such, the method may be characterized as applying a first stimulus to the subject and monitoring the subject for a response thereto. Following this first step, the method further includes applying at least a second stimulus to the subject, wherein the second stimulus is determined based on the monitored response to the first stimulus.

In certain embodiments, stimulus to the subject is done in an "irregularly irregular" manner. As such, duration of the stimulus application events, as well as duration of holiday periods between such events, varies randomly over the entire course of a treatment, or at least a portion thereof. In addition, the variation does not follow any pattern, but instead is random.

In practicing the subject methods, the applied stimulus may vary, where in certain embodiments the stimulus may be a pharmacological stimulus and/or an energetic (e.g., electrical stimulus) and/or behavioral stimulus. As such, in certain embodiments, the stimulus is a pharmacological stimulus. In other embodiments, the stimulus is an energetic stimulus. In some embodiments, the stimulus is a behavioral stimulus. In yet other embodiments, the stimulus is a combination of pharmacological and energetic stimuli. In some embodiments, the stimulus is a combination of pharmacological and behavioral stimuli. In some embodiments, the stimulus is a combination of energetic and behavioral stimuli. Accordingly, in certain embodiments, the enhancing is by administering a pharmacological agent to the subject. In yet other embodiments, the enhancing is by energetic stimulation, e.g., by employing an energy application device, such as a non-invasive or an implanted energy application device. In some embodiments, the enhancing is by administering a behavioral modulation to the subject.

Representative pharmacological agents that may find use in certain embodiments of the subject invention include pro parasympathetic agents. Pro parasympathetic agents of interest include, but are not limited to: Beta Blockers, Aldosterone Antagonists; Angiotensin II Receptor Blockers; Angiotensin Converting Enzyme Inhibitors; Statins; Triglyceride Lowering Agents; Insulin Sensitizers; Insulin Secretagogues; Insulin Analogs; Alpha-glucosidase Inhibitors; SGLT2 Inhibitors; Immunomodulators, including agents that bind/react to CD4, gp39, B7, CD19, CD20, CD22, CD401, CD40, CD40L and CD23 antigens; Sympathomimetics; Cholinergics; Calcium Channel Blockers; Sodium Channel Blockers; Glucocorticoid Receptor Blockers; Peripheral Adrenergic Inhibitors; Blood Vessel Dilators; Central Adrenergic Agonists; Alpha-adrenergic Blockers; Combination Diuretics; Potassium-sparing Diuretics; Nitrate Pathway Modulators; Cyclic Nucleotide Monophosphodiesterase (PDE) Inhibitors; Vasopressin Inhibitors; Renin Inhibitors; Estrogen and Estrogen Analogues and Metabolites; Vesicular Monoamine Transport (VMAT) Inhibitors; Progesterone Inhibitors; Testosterone Inhibitors; Gonadotropin-releasing Hormone Inhibitors; Dipeptidyl Peptidase IV inhibitors; Anticoagulants; Thrombolytics.

Instead of, or in addition to, pharmacological protocols, energetic and/or behavioral protocols may be employed in these paradoxical approaches. Useful energetic and behavioral modification that may be employed include, e.g., those described herein. In some instances, an energetic protocol (e.g., an electrical protocol) is employed to obtain the desired paradoxical decrease in sympathetic/parasympathetic activity ratio. In some instances, a behavioral protocol is employed to obtain the desired paradoxical decrease in sympathetic/parasympathetic activity ratio. As reviewed above, a number of different methods and corresponding devices and systems for applying energy to a subject or administering a behavioral modification may be adapted for use in the subject methods. For example, a number of different methods and corresponding devices and systems for applying electrical energy to a subject and which may be adapted for use in the subject invention are described, e.g., in U.S. Pat. Nos. 7,149,574; 7,711,430; and 7,363,076; as well as U.S. patent application Ser. No. 11/592,027; the disclosures of which are herein incorporated by reference.

Subjects

The methods described herein may be employed with a variety of different types of subjects, i.e., animals, where the animals are typically "mammals" or "mammalian," where these terms are used broadly to describe organisms which are within the class mammalia, including the orders carnivore (e.g., dogs and cats), rodentia (e.g., mice, guinea pigs, and rats), lagomorpha (e.g., rabbits) and primates (e.g., humans, chimpanzees, and monkeys). In many embodiments, the subjects or patients will be humans.

In some embodiments, the subject in which autonomic function is modulated has been diagnosed as having a parasympathetic bias mediated condition. In some instances, the methods may include diagnosing the subject as having a parasympathetic bias mediated condition. Diagnoses of such conditions may be made using any convenient protocol. In some instances, the subject is also one that has been determined to have an autonomic dysfunction. As used herein, the term "autonomic dysfunction" describes any disease or malfunction of the autonomic nervous system. A specific type of autonomic dysfunction of interest is parasympathetic bias. A specific type of parasympathetic bias of interest is vagal bias.

In certain embodiments modulation of at least a portion of a subject's autonomic nervous system is not performed unless one or more aspects of the autonomic nervous system are detected and indicate such modulation is necessary. One aspect that may indicate modulation is necessary is the existence of an autonomic dysfunction, such as parasympathetic bias, e.g. vagal bias.

In certain embodiments the subject has an autonomic dysfunction before diagnosis of an autonomic dysfunction (e.g. parasympathetic bias) occurs. Any suitable physical and/or chemical aspect or indicator of the autonomic nervous system may be employed by one or more of a doctor, nurse, medical professional or individual with appropriate expertise to diagnose an autonomic dysfunction.

As a non-limiting example, in some instances, a subject may have an undiagnosed food allergy condition and an undiagnosed parasympathetic bias. Such a subject may be assessed for a food allergy condition before or after being assessed for parasympathetic bias. Accordingly, in some instances, a food allergy condition may be treated, based on treating an underlying parasympathetic bias, prior to diagnosis of the food allergy condition. For example, a subject may suspect a food allergy condition, e.g., based on a dislike or general discomfort related to foods containing a particular allergen, and may be assessed for a parasympathetic bias. Upon detection of a parasympathetic bias, the subject may be treated accordingly to the methods described herein whether or not the subject has actually been diagnosed with the suspected food allergy condition.

In some instances, a subject is assessed for parasympathetic bias only after a food allergy condition is detected. In some instances, a subject is assessed for a food allergy condition only after a parasympathetic bias is detected. Accordingly, in some embodiments, a subject may be treated, e.g., according to the methods as described herein, to modulate the subject's autonomic nervous system after being diagnosed with a food allergy condition but prior to having had an acute exposure to the allergen and/or an acute response to an exposure to the allergen (including e.g., anaphylaxis).

As summarized above, in some instances, a subject has been diagnosed with one or more conditions. As a non-limiting example, in some instances, a subject may have a diagnosed food allergy condition and an undiagnosed parasympathetic bias. In such instances, the subject having the food allergy condition may be assessed for an autonomic dysfunction and, if the autonomic dysfunction is detected, then the subject may be treated for the food allergy condition, e.g., according to the methods of modulating a subject's autonomic nervous system as described herein.

Accordingly, in some embodiments, a subject may be treated, e.g., according to the methods as described herein, to modulate the subject's autonomic nervous system after being diagnosed with a food allergy condition but prior to having had an acute exposure to the allergen and/or an acute response to an exposure to the allergen (including e.g., anaphylaxis).

In some embodiments, a subject may be treated for a food allergy condition by treating an underlying parasympathetic bias. Such treatments may be performed in the absence of an acute exposure to the allergen. As used herein, the term "acute exposure to an allergen" refers to ingestion, or other contact, with the allergen outside of a medical treatment or diagnostic context to a sufficient extent to induce one or more adverse symptoms of the allergic condition. Accordingly, treatment outside of the context of an acute exposure may be employed when the subject is not exposed to the allergen and is not suffering one or more symptoms of an allergic reaction. Such treatments may be employed for various purposes including e.g., to treat a subject for an autonomic dysfunction (e.g., parasympathetic bias) underlying an allergic condition, including e.g., where such treatments prevent an allergic response and/or the occurrence of one of more symptoms of a food allergy condition upon an acute exposure of the subject to the allergen.

In some instances, a subject may be treated for an underlying parasympathetic bias during or immediately following an acute exposure to an allergen. Such treatments may, e.g., be employed to reduce one or more symptoms (e.g., the number of symptoms, the magnitude of the symptoms, or both) of the allergic reaction. Accordingly, treatments of the present disclosure applied during and/or immediately following an acute exposure to an allergen may reduce the occurrence of one or more symptoms of the food allergy as compared to the subject's response to the food allergen in the absence of the treatment.

An autonomic dysfunction in a subject may be tested for by detecting one or more aspects of the autonomic nervous system, e.g., amounts of T helper cells (Th1 and/or Th2), conduction, catecholamine levels, heart rate variability ("HRV"), action potentials, QT interval, particular hormone levels, as well as chronotropic, inotropic, and vasodilator responses. For example, in certain embodiments HRV measures such as low frequency peak ("LF"), high frequency peak ("HF"), and the LF/HF ratio may be used as indicators of different aspects of the autonomic nervous system. In certain embodiments, detection may include detecting the activity or function of a particular organ or system under the control of the autonomic nervous system. Any suitable detection means may be employed to detect relevant information about the autonomic nervous system.

These and other methods and devices for detecting one or more aspects of the autonomic nervous system potentially indicating an autonomic dysfunction that may be employed by embodiments of the subject methods include those described in U.S. Pat. Nos. 7,899,527 and 6,490,480 and U.S. patent Ser. Nos. 10/861,566 and 12/727,560.

Specific Parasympathetic Bias Mediated Conditions and Methods of Treating the Same In further describing various aspects of the invention, specific parasympathetic bias medicated conditions and methods for their treatment are now described in greater detail below.

Food Allergy Syndrome

Aspects of the invention include treating a food allergy syndrome condition in a subject. As used herein, the term "syndrome" refers to one or more symptoms that are characteristic of a specific disorder or disease. Thus, the phrase "food allergy syndrome" refers to one or more symptoms which are characteristic of or associated with a food allergy. As such, a food allergy syndrome condition is a condition associated with one or more symptoms characteristic of a food allergy. Accordingly, a food allergy syndrome condition is a condition that is related to reactions caused or exacerbated by a food allergy. Specific food allergy syndrome conditions that may be treated according to embodiments of the invention include, but are not limited to conditions having symptoms associated with the respiratory, digestive, integumentary, cardiovascular, and/or other body systems. In certain embodiments, food allergy syndrome conditions manifest as one or more symptoms, where such symptoms include, but are not limited to: bronchospasm, cough, rhinorrhea, angioedema, gastric hypermotility, urticaria, pruritis, eczema, fatigue, bradycardia, and/or hypotension. As the target condition of the methods described herein is a food allergy syndrome, the subject that is treated by methods of the invention is one that also has one or more food allergies with which the syndrome is associated.

Symptom associated with food allergy conditions may include e.g., a mild to moderate symptom (e.g., hives, itchy (especially in the mouth or ear canal), tingling in the mouth, nausea, vomiting, diarrhea, stomach pain, nasal congestion, rhinorrhea, sternutation, slight dry cough, odd taste in mouth, etc.) and/or moderate to severe symptoms (e.g., trouble swallowing, shortness of breath, wheezing, repetitive cough, cyanosis, hypotension, lightheadedness, disorientation, syncope, loss of consciousness, chest pain, a weak or "thready" pulse, anxiety (e.g., a sense of "impending doom"), anaphylaxis, constriction and tightening of the airways, shock with a sudden hypotension, rapid pulse, dizziness, circulatory collapse, swelling (especially lips, face, tongue and/or throat), abdominal pain, diarrhea, nausea, vomiting, etc.). Reduction of symptoms may include a reduction in the magnitude of the symptom, a reduction in the frequency of the symptom, a reduction in the duration of a symptom, a reduction in the number of symptoms, and/or combinations thereof.

Common food allergens to which a subject may be allergic include but are not limited to e.g., nuts and seeds (e.g., almond, brazil nut, cashew, chestnut, cocoa, coconut, cotton seed, flax seed, linseed, hazelnut, mustard, pecan, pine nut, poppy seed, sesame, sunflower seed (botanically a fruit), walnut, etc.); grains and cereals (e.g., barley, buckwheat, maize, oat, rice, rye, wheat, etc.); legumes (e.g., castor bean, chickpea, lentil, lupine, peanut, soybean, etc.), fruits (e.g., acerola, apple, apricot, avocado, banana, cherry, coconut, date, fig, garden plum, grape, kiwi fruit, lychee, mango, melon, peach, pear, persimmon, pineapple, pomegranate, strawberry, tomato, etc.); vegetables (e.g., cabbage, carrot, celery, zucchini, garlic, lettuce, potato, turnip, etc.); herbs and spices (e.g., aniseed, chamomile, celery, garlic, etc.); shellfish and snails (e.g., abalone, crab, lobster, oyster, shrimp, snail, squid, etc.); fish (e.g., Alaskan pollock, carp, cod, mackerel, salmon, tuna, etc.); chicken egg; bovine milk; and the like.

As summarized above, subjects treated according to the herein described methods may or may not have been previously diagnosed with a food allergy condition. Methods of diagnosing food allergy conditions vary. Useful allergy assessments include but are not limited to e.g., oral food allergy challenge (OFC) (e.g., open-food challenge, single-blind food challenge, double-blind, placebo-controlled food challenge (DBPCFC), and the like); skin prick tests; blood tests; trial elimination diet tests; and the like. Useful evaluations are further described in "*Guidelines for the Diagnosis and Management of Food Allergy in the United States*" (Boyce et al., *J Allergy Clin Immunol*. (2010) 126(6 0): S1-58); the disclosure of which is incorporated herein by reference in its entirety. In some embodiments, food allergy assessment may be employed to diagnose a subject with a food allergy condition or a subject may have been previously diagnosed with a food allergy condition according to a food allergy assessment previously performed. In some instances, useful methods of diagnosing a food allergy condition may include an antigen challenge.

As used herein, the term "antigen challenge" generally refers to exposing a subject to an antigen to which the subject may have an allergy. The subject may be known to have an allergy to the antigen or the subject may be suspected of having an allergy to the antigen. With respect to food allergies, such an antigen challenge may be performed as an oral food challenge (OFC). In an OFC, a subject may be administered an antigen, to which the subject has a known or suspected allergy, for oral ingestion. Methods of administering an oral food challenge may vary. For example, in some instances, a subject may be administered the antigen (e.g., peanut, gluten, etc.) in an isolated, purified or enriched form, including but not limited to e.g., an extract or concentrate of a particular portion of the food allergen, such as e.g., peanut protein extract, peanut protein concentrate, gliadin, etc. In some instances, a subject may be administered the antigen in food form, e.g., in a whole, cooked, uncooked, or raw form, for ingestion by normal means. During an OFC a subject may or may not be administered other (i.e., non-antigen-containing) foodstuffs.

During a typical OFC, an OFC administrator (e.g., a healthcare professional, an allergist, a physician, a technician, nurse, etc.) may feed the suspected or known antigen, or food containing the suspected of known antigen, in one or more measured doses. The OFC administrator will generally begin with small amounts unlikely to trigger a symptomatic response in the subject. In some instances, with each dose, the OFC administrator or other healthcare professional will observe the subject for a period of time, evaluating the subject for one or more, including any, signs of a reaction. When no significant symptoms are observed, the challenge dose may be gradually increased and re-administered. In some instances, an OFC may be administered as a double-blind, placebo-controlled food challenge (DBPCFC), a single-blinded food challenge, or an open-food challenge.

Depending on the severity and the particular circumstances of the OFC, in some instances, when the subject displays one or more signs of a reaction the food challenge may be halted or terminated. Given the controlled nature of OFCs, observed reactions are generally mild, such as e.g., as flushing or hives, and severe reactions are uncommon. In instances where a subject displays a moderate and/or severe reaction, the subject may be administered one or more medications to relieve one or more symptoms if necessary or desired.

In some instances, antigen challenges are given to subjects not already known to have a food allergy. In some instances, antigen challenges are given to subjects already known to have a food allergy. Subject known to have a food allergy may be administered an antigen challenge for a variety of reasons including but not limited to e.g., to assess the severity of the food allergy condition of the subject, as part of a tolerance therapy, and the like.

In some instances, methods of the present disclosure may include an antigen challenge. An antigen challenge may be included in the methods of the present disclosure for various purposes, including but not limited to e.g., as an aspect of a course of therapy for a food allergy condition, to assess effectiveness of the treatment provided, to train a subject on a behavioral modification, to calibrate a modification (e.g., an energetic or pharmacological modification), to diagnosis a food allergy condition, or the like.

Antigen challenges may be administered at any convenient point during a course of therapy including e.g., before, during, and/or after, a modulation performed according to the methods described herein. For example, in some instances, a subject may be administered an antigen challenge before a modulation, including but not limited to e.g., as a means of assessing the subject for the food allergy and/or assessing the severity of a subject's food allergy condition. In some instances, a subject may be administered an antigen challenge during the modulation, including but not limited to e.g., as a means of causing the modulation to be co-present with the allergen. In some instances, a subject may be administered an antigen challenge after modulation, including but not limited to e.g., as a means of assessing the subject for the food allergy and/or assessing the severity of a subject's food allergy condition and/or assessing the effectiveness of the treatment.

In instances where an antigen challenge is employed, a subject method may include only one antigen challenge or multiple antigen challenges, including where each of the plurality of antigen challenges are administered at various points in the treatment schedule, including before, during, and/or after a modulation as described herein. For example, where multiple antigen challenges are employed, in some instances, an antigen challenge may be performed before and/or during each of the modulations, including where the multiple modulations are all of the same type or different types.

In some instances, useful assessments may include one or more in vitro assessments, e.g., performed on a sample obtained from the subject. Useful in vitro assessments may include in vitro allergy testing, such as but not limited to e.g., in vitro tests for detecting allergen-specific IgE. In vitro allergy testing may include collecting a sample from the subject, e.g., a blood and/or serum sample, and evaluating the presence of an analyte, e.g., allergen-specific IgE, in the sample to assess the subject for the food allergy condition.

Such assessments may be qualitative or quantitative depending on the particular context. For example, in some instances, an assessment, including allergy assessments of the subject (e.g., an OFC assessment) or an in vitro assessment (e.g., allergen-specific IgE evaluation), may indicate an improvement in the subject's food allergy condition. Such improvements may be qualitative or quantitative. For example, in some instances, assessing a food allergy condition of a subject may indicate a quantitative improvement, such as e.g., at least a 5% improvement in the food allergy condition of the subject. Measured improvements may vary according to the method employed to assess a subject's food allergy condition. For example, in some instances, an assessment may indicate at least a 5% increase in food antigen tolerance following a method of treatment as described herein, e.g., as measured by an OFC. In some instances, an assessment may indicate at least a 5% decrease in the presence allergen-specific IgE following a method of treatment as described herein, e.g., as measured by an in vitro assessment.

Various assessments may be employed to measure one or more conditions of a subject before, during, and/or after a modulation as described herein. In some instances, a subject may be continuously or semi-continuously assessed (i.e., monitored) during one or more, including all, portions of a method of treatment described herein.

The subject methods find use in a variety of applications in which it is desired to treat a subject for a food allergy syndrome condition, e.g., a food allergy syndrome condition that may be influenced by an abnormality in the subject's autonomic nervous system (e.g., a parasympathetic bias). In such methods, at least a portion of a subject's autonomic nervous system is modulated in a manner suitable to treat the subject for the condition, e.g., in a manner to decrease the parasympathetic activity/sympathetic activity ratio in certain embodiments, e.g., as applied to a portion of the respiratory, digestive, integumentary, cardiovascular, and/or other body systems.

The subject methods find use in the treatment of a variety of different food allergy syndrome conditions in which an abnormality in a subject's autonomic nervous system exists. By treatment is meant both a prevention and/or at least an amelioration of the symptoms associated with the condition afflicting the subject is achieved, where amelioration is used in a broad sense to refer to at least a reduction in the magnitude of a parameter, e.g., symptom, associated with the food allergy syndrome condition being treated. As such, treatment also includes situations where the condition, or at least symptoms associated therewith, are completely inhibited, e.g. prevented from happening, or stopped, e.g. terminated, such that the subject no longer suffers from the food allergy syndrome condition, or at least the symptoms that characterize the condition.

As noted above, abnormalities in a subject's autonomic nervous system include those characterized by an abnormally high parasympathetic activity or abnormally low parasympathetic activity and/or an abnormally high sympathetic activity or abnormally low sympathetic activity. Certain abnormalities may be characterized by having normal activity in one of the systems of the autonomic nervous system (the parasympathetic system or sympathetic system), but which may have abnormal activity in the other system (the parasympathetic system or sympathetic system).

The subject methods find use in the treatment of a variety of different food allergy syndrome conditions. Such food allergy syndrome conditions include, but are not limited to: conditions associated with the respiratory system including bronchospasm, cough, and rhinorrhea; conditions associated with the digestive system including gastric hypermotility; conditions associated with the integumentary system including angioedema, urticaria, pruritis, atopic dermatitis, and eczema; conditions associated with the circulatory system including fatigue, bradycardia, and hypotension; and combinations thereof.

In some instances, methods of the invention may also result in treatment of symptoms of the food allergy for which the syndrome is associated. Such symptoms may vary, and may include: difficulty swallowing, hives, vomiting, shortness of breath, stomach cramps, runny nose, patches of scaly or itchy skin, nausea, nasal congestion, lightheadedness, rash, diarrhea, fainting, abdominal pain, and swelling of the eyelids, face, lips, tongue or other areas, low blood pressure, blocked airways, and combinations thereof.

Conditions Normally Treated with Steroids

Aspects of the invention include using an epinephrine active agent for treatment of conditions normally treated with steroids. By epinephrine active agent is meant epinephrine or a functional equivalent thereof, e.g., an analogue, derivative, etc. Epinephrine is a chiral molecule having the structure:

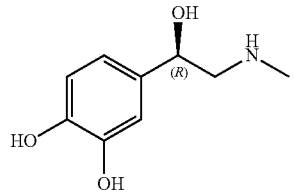

In some instances, the epinephrine active agent is epinephrine free base or a salt thereof, e.g., epinephrine hydrochloride, epinephrine bitartrate, etc.

Conditions normally treated with steroids which may be treated with an epinephrine active agent include, but are not limited to: ocular conditions, e.g., retinopathy, uveitis, a neovascularization disorder such as choroidal neovascularization, posterior segment neovascularization, or iris neovascularization, macular degeneration, macular edema, vein occlusion, ocular ischemic syndrome, orbital inflammatory diseases, surgically induced inflammation, thyroid-related orbital inflammatory disease, endophthalmitis, pain from a blind eye, hypotony, ocular vascular tumors, serous retinal detachment, chronic retinal detachment, idiopathic parafoveal telangectasia, iridocyclitis, papillitis, retinal vasculitis, keratitis, corneal transplant rejection, corneal melts, autoimmune diseases of the cornea and sclera, autoimmune-related eye and orbital diseases, chalazion, orbital pseudo-tumor, scleritis, and episcleritis; diseases of the skin or mucous membranes, which include but are not limited to the mouth, nasopharynx, respiratory tract, and gastrointestinal system, such as dermatitis, eczema, insect bites, lesions, ulcers, hemangiomas, vascular skin tumors, keloids, psoriasis, hypertrophic scars, traumatic scars, autoimmune skin disease, alopecia areata and other autoimmune disease that leads to hair loss, discoid lupus, esophageal strictures, and subglottic stenosis; musculoskeletal diseases, which include without limitation bursitis, synovitis, tendonitis, capsulitis, arthritis (including without limitation osteoarthritis, psoriatic arthritis, idiopathic arthritis, and rheumatoid arthritis), epicondylitis, back pain, and fasciitis; asthma, clinical inflammation, epicondylitis, endocrine disorders, lupus, rheumatic carditis, herpes zoster ophthalmicus, colitis, irritable bowel syndrome, ulcerative colitis, gastroenteritis, Crohn's disease, hemolytic anemia, leukemia, lymphoma, and rhinitis. In some embodiments, the methods of using epinephrine in treating conditions normally treated by steroids are not methods in which epinephrine is already known to treat the condition as of the filing date of this application.

Conditions Normally Treated with Epinephrine

Aspects of the invention include using a steroid active agent for treatment of conditions normally treated with epinephrine. By steroid active agent is meant a compound having four joined cycloalkane rings and having a suitable activity. Steroids of interest include, but are not limited to, glucocorticoids, where glucocorticoid of interest include, but are not limited to, dexamethasone, fluoromethalone, medrysone, betamethasone, triamcinolone, triamcinolone acetonide, prednisone, prednisolone, hydrocortisone, rimexolone, prednicarbate, deflazacort, halomethasone, tixocortol, prednylidene, prednival, paramethasone, methylprednisone, meprednisone, mazipredone, isofluopredone, halopredone acetate, halcinonide, formocortal, flurandrenolide, fluprednisone, fluprednidine acetate, fluperolone acetate, fluocortolone, fluocortin butyl, fluocinonide, fluocinolone acetonide, flunisolide, flumethasone, fludrocortisone, fluclorinide, enoxolone, difluprednate, diflucortolone, diflorasone diacetate, desoximetasone, desonide, descinolone, cortivazol, corticosterone, cortisone, cloprednol, clocortolone, clobetasone, clobetasol, chloroprednisone, cafestol, budesonide, beclomethasone, amcinonide, allopregnane acetonide, aldlometasone, 21-acetoxypregnenolone, tralonide, diflorasone acetate, deacylcortivazol, RU-26988, deacyulcortivazol oxetanone, triamcinolone acetonide, prednisolone, prednisolone acetate, rimexolone, flurormethalone, and flurometalone acetate; hydrocortisoids; angiostatic steroids, such as hydrocortisone, tetrahydrocortisol-S, 11α-epihydrocotisol, cortexolone, 17α-hydroxyprogesterone, corticosterone, desoxycorticosterone, testosterone, estrone, dexamethasone, triamcinolone, and 6α-fluoro-17,21-dihydroxy-16β-methyl-pregna-4,9,(11)-diene-3,20-dione, anecortave acetate; triamcinolones ((11β, 16α)-9-fluoro-11,17,18,21-dihydroxy-pregna-1,4-diene-3, 20-dione) or one of its derivatives such as, but not limited to, triamcinolone diacetate (10, 16α)-16,21bis(acetyloxy)-9-fluoro-11,17-dihydroxypregna-1,4-diene-3,20-dione); triamcinolone hexacetonide ((11β,16α)-21-(3,3dimethyl-1-oxobutoxy)-9-fluoro-11-hydroxy-di-hydroxy-16,17-[1-methyldethylidenebis(oxy)]-pregna-1,4-diene-3,20-dione), or triamcinolone betonide ((11β,16α)-21-[3-benzoylamino-2methyl-1-oxypropoxyl-9-fluoro-1-1-hydroxy-16,17-[1-methyldethylidenebis(oxy)]-pregna-1,4-diene-3,20-dione)-, triamcinolone acetonide ((11β,16α)-9-fluoro-11,21-dihydroxy-16,17-[1-methyld-ethylidenebis(oxy)]-pregna-1,4-diene-3,20-dione)).

Conditions normally treated with epinephrine which may be treated with an steroid active agent include, but are not limited to: disorders which are mediated by an alpha- or beta-receptor, such as blood pressures, vascular system conditions, the heart conditions; neurological disorders such as schizophrenia, Parkinson's disease and attention-deficit hyperactivity disorder; cardiac disorders, such as hypotension, forward failure, backward failure and congestive heart failure; vascular disorders, such as shock, hypotension, hemorrhage, and disorders associated with anesthesia; respiratory disorders, such as nasal congestion, oral and nasal inflammation and swelling (such as caused by cold or flu), chronic obstructive pulmonary disease, asthma, emphysema, and bronchospasm; gastrointestinal disorders, such as colic and Crohn's disease; anaphylaxis; interstitial cystitis; overactive bladder syndrome; premature labor; myasthenia gravis; glaucoma; dilation of pupils; and weight reduction. The term "anaphylaxis," as that term is used herein, refers to a broad class of immediate-type hypersensitivity and anaphylactic conditions well known to those skilled in the art including, but not limited to, anaphylactoid reactions, anaphylactic shock, idiopathic anaphylaxis, allergen induced anaphylaxis, exercise induced anaphylaxis, exercise-induced food-dependent anaphylaxis, active anaphylaxis, aggregate anaphylaxis, antiserum anaphylaxis, generalized anaphylaxis, inverse anaphylaxis, local anaphylaxis, passive anaphylaxis, reverse anaphylaxis, and systemic anaphylaxis. An "episode" of anaphylaxis, as that term is used herein, refers to a continuous manifestation of anaphylaxis in a patient. In some embodiments, the methods of using a steroid active agent in treating conditions normally treated by epinephrine are not methods in which a steroid is already known to treat the condition as of the filing date of this application.

Diagnosis and/or Prevention of Anaphylaxis

Aspects of the invention include methods of diagnosing and/or preventing anaphylaxis in a subject. The term "anaphylaxis" refers to an allergic condition that is rapid in onset and may be characterized by a number of symptoms, including itchy rash, throat swelling, and low blood pressure. The anaphylactic condition may result from a number of different causes, such as foods, medications, insect bites or stings, etc.

In some instances, autonomic function may be monitored in a subject, where occurrence of autonomic dysfunction (e.g., vagal bias) may be used to predict that a patient will have or is having an anaphylactic attack. The monitoring may be continuous and "real-time" in some instances, such that a subject is continuously monitored for the occurrence of autonomic dysfunction. Autonomic function (and therefore dysfunction thereof, e.g., vagal bias) may be monitored using any convenient protocol. An autonomic dysfunction in a subject may be tested for by detecting one or more aspects of the autonomic nervous system, e.g., amounts of T helper cells (Th1 and/or Th2), conduction, catecholamine levels, heart rate variability ("HRV"), action potentials, QT interval, particular hormone levels, as well as chronotropic, inotropic, and vasodilator responses. For example, in certain embodiments HRV measures such as low frequency peak ("LF"), high frequency peak ("HF"), and the LF/HF ratio may be used as indicators of different aspects of the autonomic nervous system. In certain embodiments, detection may include detecting the activity or function of a particular organ or system under the control of the autonomic nervous system. Any suitable detection means may be employed to detect relevant information about the autonomic nervous system. These and other methods and devices for detecting one or more aspects of the autonomic nervous system potentially indicating an autonomic dysfunction that may be employed by embodiments of the subject methods include those described in U.S. Pat. Nos. 7,899,527 and 6,490,480 and U.S. patent Ser. Nos. 10/861,566 and 12/727,560. Employing autonomic function as an indicator that a subject is or will suffer from an anaphylactic attack may be used to predict the presence or occurrence of such an attack before other symptoms, e.g., as described above, may occur.

In some instances, these methods further include treating the subject for the anaphylactic attack prior to the occurrence of other symptoms, such as itchy rash, throat swelling, and low blood pressure. For example, where one has a subject that may be in danger of suffering from an anaphylactic attack, the subject can be monitored for autonomic dysfunction. For instance, continuous heart rate monitoring (proxy for vagal bias) may be employed for a subject who may be receiving oral immunotherapy (OIT) as a potential heralding sign of adverse immunologic reactions. If autonomic dysfunction is at least predicted to present, e.g., through diagnosis such as described above, interventional therapy for the anaphylactic attack, e.g., administration of epinephrine, may be employed to at least reduce the severity of one or more other symptoms of the attack (such as described above), if not prevent the occurrence of these one or more other symptoms of the attack.

In some instances, a closed-loop system or device may be employed. For example, a body associated device, e.g., an implanted or topical device, may be employed in such instances, where the device is configured to receive autonomic function data and, upon detection of autonomic dysfunction, administer an appropriate therapy, e.g., epinephrine, to the subject. The device may also be configured to obtain the autonomic function data. The device may be configured for long term association with the body of a subject, and may include additional components as desired, e.g., processors, power sources, etc.

Determining Treatment Protocol

Methods according to certain embodiments include determining a treatment protocol for a subject having a parasympathetic bias mediated condition, e.g., a predicted adverse response to a stimulus (such as therapeutic agent administration, nutritional ingestion, etc.). A "treatment protocol" for a subject having a target condition is a course of one or more actions which are taken to alleviate the condition or symptoms of the condition in the subject. The course of one or more actions which are taken to alleviate the condition or symptoms of the condition may include not taking action or not taking immediate action to treat the condition.

A treatment protocol for a subject having a target condition may include assessing whether the subject has an autonomic dysfunction (e.g., vagal bias). Such a determination also may include assessing the degree of autonomic function in a subject. The assessment of whether the subject has an autonomic dysfunction or the degree of autonomic dysfunction may be conducted using any appropriate methods including any of the methods described herein including detecting one or more aspects of the autonomic nervous system, e.g., amounts of T helper cells (Th1 and/or Th2), conduction, catecholamine levels, heart rate variability ("HRV"), action potentials, QT interval, particular hormone levels, as well as chronotropic, inotropic, and vasodilator responses. For example, in certain embodiments HRV measures such as low frequency peak ("LF"), high frequency peak ("HF"), and the LF/HF ratio may be used as indicators of different aspects of the autonomic nervous system. In certain embodiments, detection may include detecting the activity or function of a particular organ or system under the control of the autonomic nervous system. Any suitable detection means may be employed to detect relevant information about the autonomic nervous system potentially indicating an autonomic dysfunction including those described in U.S. Pat. Nos. 7,899,527 and 6,490,480 and U.S. patent application Ser. Nos. 10/861,566 and 12/727,560; the disclosures of which are herein incorporated by reference.

In some embodiments, assessing a subject may include one or more dynamic measurements of a subject, e.g., based on dynamic biometric data obtained from the subject. The phrase "biometric data" is employed to refer to a measure of a biometric parameter that relates to the physiology of a living organism, e.g., as described below. As such, the biometric parameter which is employed to obtain the biometric data may be a parameter that provides information about an organism's vital functions, including growth and development, the absorption and processing of nutrients, the synthesis and distribution of proteins and other organic molecules, the functioning of different tissues, organs, and other anatomic structures; the psychological and/or behavioral state of the subject, e.g., mental and/or cognitive state of the subject, which may be subjective or objective, self-reported or third party observed, as desired; etc.

Biometric parameters that are measured may vary widely, where examples of such parameters include physiological, chemical, electrical, behavioral, psychological, etc., based parameters, as well as variations and derivatives thereof. Biometric parameters of interest include, but are not limited to: physical parameters, e.g., blood pressure, orthostatic hypotension, pulse pressure, heart rate, heart rate variability (HRV), heart rate recovery, resting heart rate, respiration rate, forced expiratory volume, forced vital capacity, temperature, core temperature, galvanic skin response, gastrointestinal motility, sleep cycle, VO2 max, bone density, weight, body mass index (BMI), bone density, waist to hip ratio, waist circumference, other obesity measures (e.g., volume displacement, Dual Energy X-ray Absorptiometry (i.e., DEXA), etc.), baroreceptor sensitivity, oxygen saturation, nervous system activity measurements, including electrical potential measurements, such as spontaneous electrical potential measurements, e.g., EEG, EMG EKG, evoked electrical potential measurements, e.g., sensory evoked potentials (such as auditory invoked potentials (e.g., brain stem evoked response or potential (ABER or ABEP), visual evoked potentials, tactile or somatosensory evoked potentials, laser evoked potentials), motor evoked potentials, etc.; nerve conduction measures, e.g., motor NCS, sensory NCS, F-wave study, H-reflex study, spf-NCS, etc.; and the like, and combinations thereof; sample analysis obtainable parameters, e.g., pH level, cortisol level, ACTH level, Epinephrine/Norepinephrine level, oxygen saturation, insulin, glucose, inflammatory/immune markers, DNA methylation, DNA double strand breaks, clock genes/factors, oxidative stress, telomere status, gut biome, melatonin level, adenosine level, creatinine, urea nitrogen, c-reactive protein, hemoglobin, triglycerides, lipoproteins, apoloipoprotein B100/A1 ratio, white blood cell count, cholesterol, oxygen saturation, and the like, and combinations thereof. Dynamic biometric data may be made up of information about a single type of biometric parameter, or two or more different types of biometric parameters. The biometric data employed in methods of the invention may thus be made up of information obtained by measuring or assessing one or more biometric parameters, such as the ones listed above.

As summarized above, the biometric data that is obtained and employed may be dynamic biometric data. By "dynamic biometric data" is meant biometric data that incorporates some type of change component, as opposed to static biometric data. The change component may vary widely, where examples of change components include, but are not limited to components that are: temporal and/or in response to an applied stimulus and/or in response to withdrawal of stimulus and/or in response to a change in the contextual environment of the subject. For example, the dynamic biometric data that is obtained may be biometric data obtained over a given period of time. The given period of time may vary, ranging in some instances from 0.1 seconds to 24 hours, such as 1 second to 12 hours, e.g., 1 second to 1 hour, including 1 second to 1 minute. Where the dynamic biometric data is data obtained over a given period of time, the data may be obtained continuously over that period of time or at one or more distinct points during that period of time. For example, the biometric parameter(s) that is monitored in order to obtain biometric data may be monitored continuously during the given period of time, i.e., it may be obtained in an uninterrupted manner, i.e., without cessation, during the given period of time. Alternatively, the biometric parameter(s) that is monitored in order to obtain biometric data may be monitored intermittently during the given period of time, i.e., it may be obtained at one or more points over the given period of time, with an interval between points at which it is not obtained. In some embodiments, the interval may vary, ranging, for example, from 0.01 sec to 60 minutes or longer, such as 0.1 to 60 s. In some instances, the dynamic biometric data is obtained by evaluating a biometric parameter for a rate of change over a period of time. As such, methods may include obtaining information about the speed at which a biometric parameter of interest changes over a given period of period of time. Obtaining dynamic biometric data as described above provides for numerous benefits, including increases in temporal resolution, as compared to single point in time data. Dynamic biometric data as obtained herein provides a truer and more meaningful measure of the biometric value(s) of interest, as compared to single point in time measurements.

Dynamic biometric data of interest also include biometric data that is obtained by evaluating a biometric parameter for a change in response to an applied stimulus. Such biometric data may include data that is obtained before and/or after application of the stimulus to the subject. In some instances, the biometric data may be obtained over a given period of time that spans or follows the application of the stimulus to the subject. This type of biometric data may be viewed as biometric data that is obtained over a given period of time in conjunction with application of a stimulus to the subject being evaluated. The applied stimulus may vary, where stimuli of interest include physical stimuli and chemical stimuli. Physical stimuli of interest include, but are not limited to, change in orientation of the subject, exercise, change in temperature experienced by the subject or a portion thereof, and the like. Chemical stimuli of interest include, but are not limited to, administration of various active agents, e.g., orally, topically, by injection or other type of administration route, where active agents of interest include, but are not limited to: sugars, starches, stimulants, and the like.

Dynamic biometric data of interest also include biometric data that is obtained by evaluating a biometric parameter for a change in response to withdrawal of a stimulus. Such biometric data may include data that is obtained before and/or after withdrawal (e.g., blockage) of the stimulus to the subject. In some instances, the biometric data may be obtained over a given period of time that spans or follows the withdrawal of the stimulus to the subject. This type of biometric data may be viewed as biometric data that is obtained over a given period of time in conjunction with withdrawal of a stimulus to the subject being evaluated. The withdrawn stimulus may vary, where stimuli of interest include physical stimuli and chemical stimuli. Physical stimuli of interest include, but are not limited to, change in orientation of the subject, exercise, change in temperature experienced by the subject or a portion thereof, and the like. Chemical stimuli of interest include, but are not limited to, administration of various active agents, e.g., orally, topically, by injection or other type of administration route, where active agents of interest include, but are not limited to: sugars, starches, stimulants, and the like.

Dynamic biometric data of interest also include biometric data that is obtained by evaluating a biometric parameter for a change in response to modulation of the contextual environment of the subject. By contextual environment of the subject is meant the perceived environment of the subject. Such biometric data may include data that is obtained before and/or after the modulation in the contextual environment of the subject. In some instances, the biometric data may be obtained over a given period of time that spans or follows the modulation of the contextual environment of the subject. This type of biometric data may be viewed as biometric data that is obtained over a given period of time in conjunction with modulation of the contextual environment of the subject. The modulation of the contextual environment of the subject may vary, where contextual modulations of interest include, but are not limited to, change in day and night duration, change in temperature, change in humidity, change in elevation, change in atmosphere, and the like.

Dynamic biometric data of interest also include biometric data that is obtained by evaluating a biometric parameter for a change in response to modulation of the behavioral aspect of the subject. By behavioral aspect of the subject is meant an observable activity of the subject. Such biometric data may include data that is obtained before and/or after the modulation of the behavioral aspect of the subject. In some instances, the biometric data may be obtained over a given period of time that spans or follows the modulation of the behavioral aspect of the subject. This type of biometric data may be viewed as biometric data that is obtained over a given period of time in conjunction with modulation of the behavioral aspect of the subject. The modulation of the behavioral aspect of the subject may vary, where behavioral modulations of interest include, but are not limited to, dietary changes, sleep pattern changes, activity level changes, and the like.

As reviewed above, a variety of different biometric parameters may be measured to obtain the dynamic biometric data. The method by which the biometric data is obtained may vary depending on the nature of the biometric parameter that is monitored. In some instances, the method employed to obtain the biometric data includes physically monitoring the subject to obtain the dynamic biometric data. For example, physical monitoring of the subject may be employed where the biometric parameter is one or more of blood pressure, orthostatic hypotension, pulse pressure, heart rate, heart rate variability (HRV), heart rate recovery, resting heart rate, respiration rate, forced expiratory volume, forced vital capacity, temperature, core temperature, galvanic skin response, gastrointestinal motility, sleep cycle, VO2 max, bone density, weight, body mass index (BMI), bone density, waist to hip ratio, waist circumference, other obesity measures (e.g., volume displacement, Dual Energy X-ray Absorptiometry (i.e., DEXA), etc.), baroreceptor sensitivity, oxygen saturation, nervous system activity measurements, including electrical potential measurements, such as spontaneous electrical potential measurements, e.g., EEG, EMG EKG, evoked electrical potential measurements, e.g., sensory evoked potentials (such as auditory invoked potentials (e.g., brain stem evoked response or potential (ABER or ABEP), visual evoked potentials, tactile or somatosensory evoked potentials, laser evoked potentials), motor evoked potentials, etc.; nerve conduction measures, e.g., motor NCS, sensory NCS, F-wave study, H-reflex study, spf-NCS, etc.; and combinations thereof. Any convenient protocol for physically monitoring a subject for one or more of the above biometric parameters may be employed, and methods for physically monitoring each are known in the art. For example, where the biometric parameter of interest is HRV, the physical monitoring may include measures such as low frequency peak ("LF"), high frequency peak ("HF"), and the LF/HF ratio to determine HRV and obtain the HRV derived biometric data.

In some embodiments, the dynamic biometric data is obtained by a method that includes analyzing a sample from the subject to obtain the dynamic biometric data. The sample that is analyzed may vary, where samples of interest include, but are not limited to: urine, blood, serum, plasma, saliva, semen, prostatic fluid, nipple aspirate fluid, lachrymal fluid, perspiration, feces, cheek swabs, cerebrospinal fluid, cell lysate samples, amniotic fluid, gastrointestinal fluid, biopsy tissue (e.g., samples obtained from laser capture microdissection (LCM)), and the like. The sample can be a biological sample or can be extracted from a biological sample derived from humans, animals, and the like, and may employ conventional methods for the successful extraction of DNA, RNA, proteins and peptides. In certain embodiments, the sample is a fluid sample, such as a solution of analytes in a fluid. The fluid may be an aqueous fluid, such as, but not limited to water, a buffer, and the like. Biometric parameters that may be monitored by evaluating a sample from the subject include, but are not limited to: pH level, cortisol level, ACTH level, Epinephrine/Norepinephrine level, oxygen saturation, insulin, glucose, inflammatory/immune markers, DNA methylation, DNA double strand breaks, clock genes/factors, oxidative stress, telomere status, gut biome, melatonin level, adenosine level, creatinine, urea nitrogen, c-reactive protein, hemoglobin, triglycerides, lipoproteins, apoloipoprotein B100/A1 ratio, white blood cell count, cholesterol, oxygen saturation, and combinations thereof.

Any convenient protocol for physically monitoring a subject for one or more of the above biometric parameters may be employed, and methods for testing a sample for monitoring each are known in the art. In some instances, the dynamic biometric data is obtained by both physically monitoring the subject and by assaying a sample from the subject, e.g., as described above.

After an assessment of whether the subject has an autonomic dysfunction is conducted, a determination of a treatment protocol for the subject for the target condition based on whether the subject has an autonomic dysfunction is made. The treatment protocol may include modulating autonomic function by modulating at least one portion of the subject's autonomic nervous system. As described above, modulating autonomic function may include treating the subject using any method or device, or a combination of the methods and/or devices, described or incorporated by reference herein. Such methods and devices specifically include, but are not limited to, those related to treatment using an energetic (e.g., electrical) or pharmacological or behavioral means. The determination in such instances may also include, or alternatively include, a recommendation to avoid circumstances that enhance parasympathetic bias, e.g., vagal bias, in the subject. The determination may also include, in some instances, a prescription for other treatment modalities, e.g., oral immunotherapy, in the subject.

The treatment protocol may also include specifically excluding autonomic function modulation if the subject does not have an autonomic dysfunction (e.g., vagal bias) or if the determining professional(s) determine modulation is unnecessary. In specifically excluding autonomic function modulation, a determination may be made to not perform autonomic function modulation of the subject if the subject does not have an autonomic dysfunction. Such a determination may include a determination that oral immunotherapy is sufficient to treat the food allergy.

The assessment and determination steps, e.g., as described above, may be conducted by one or more of a doctor, nurse, medical professional or individual with appropriate expertise. The assessing professional(s) may be the same as or different from the determining professional(s), e.g., as desired.

In certain embodiments, a computational system configured to perform the determination based on appropriate input is employed. Such as system may be configured to receive one or more data inputs regarding the subject and, based on such inputs, output to a user a treatment protocol, e.g., as described above. As summarized above, such output may induce a modulation of a subject's autonomic nervous system, including where the modulation is induced in an open-loop or close-loop manner.

An example of such an embodiment is where a potential adverse reaction to a given stimulus may occur if the subject has a parasympathetic, e.g., vagal, bias. For example, certain therapeutic agents have known high incidences of anaphylaxis, anaphylactoid reactions, or allergic reactions. Examples of such agents include, but are not limited to: β-lactam antibiotics (e.g., penicillin), aspirin, NSAIDs, chemotherapeutic agents, vaccines, protamine and herbal preparations. Prior to administration of such agents, the subject may be screened for the presence of parasympathetic, e.g., vagal, bias. If the subject is found to have such a bias, a suitable treatment protocol may be determined, e.g., to not administer the therapeutic agent, to administer a different agent with a reduced risk of the adverse effect, or to modulate the autonomic nervous system of the subject, e.g., as described above, to remove the bias prior to administration of the agent. For example, HRV may be employed in some instances as a measure of parasympathetic bias. In subjects with normal HRV, a determination may be made that therapeutic agents may be employed at normal or even higher dosages. In subjects determined to have low HRV (and therefore parasympathetic bias) a determination may be made to monitor the patient for side effects following administration of a therapeutic agent, or administration of lower dosages of such agents, or administration of other therapeutic agents not associated with side effects, e.g., as described further above.

Devices

A number of different devices and systems may be employed in accordance with the subject invention. Devices and systems which may be adapted for use in the subject invention include, but are not limited to, devices and systems for applying at least one pharmacological agent to a subject, devices and systems for applying energy (including e.g., electrical energy) to a subject, and devices and systems for inducing a behavioral modulation. Also included are devices and systems that employ two or more modalities, including e.g., devices and systems for applying at least one pharmacological agent to a subject and at least one energetic modulation to a subject, devices and systems for applying at least one pharmacological agent to a subject and at least one behavioral modulation to a subject, devices and systems for applying at least one energetic modulation to a subject and at least one behavioral modulation to a subject, as well as devices and systems for applying at least one pharmacological agent, at least one energetic modulation and at least one behavioral modulation to a subject.

Devices and Systems for Applying Pharmacological Agent(s)

Different devices and systems for applying one or more pharmacological agents to a subject which may be adapted for use in the subject invention include embodiments configured to deliver pharmacological agent(s) using any of the methods described above. A device for applying one or more pharmacological agents to modulate autonomic function is a "pharmacological modulator".

Embodiments may include an implantable or external pharmacological delivery device such as, but not limited to, pumps, epidural injectors, syringes or other injection apparatus, catheter and/or reservoir operatively associated with a catheter, etc. For example, in certain embodiments a delivery device employed to deliver at least one pharmacological agent to a subject may be a pump, syringe, catheter or reservoir operably associated with a connecting device such as a catheter, tubing, or the like. Containers suitable for delivery of at least one pharmacological agent to a pharmacological agent administration device include instruments of containment that may be used to deliver, place, attach, and/or insert the at least one pharmacological agent into the delivery device for administration of the pharmacological agent to a subject and include, but are not limited to, vials, ampules, tubes, capsules, bottles, syringes and bags.

In some embodiments, the device for applying one or more pharmacological agents includes a sensor for detecting a food allergy syndrome, condition, symptom and/or instigator. As used herein, an "instigator" is an aspect that causes or aggravates a food allergy syndrome condition and/or symptom. A sensor may take the form of an electrode or the like and may be configured specifically to detect one or more symptoms of a food allergy condition. Signals received by such a sensor may be amplified before further processing. A sensor may also take the form of a device capable of detecting nerve compound action potentials or may take the form of a transducer that includes an electrode with an ion selective coating applied which is capable of directly transducing the amount of a particular transmitter substance or its breakdown by-products. More detailed descriptions of sensors that may be employed in the practice of the subject invention, and other examples of sensors that may be employed are disclosed in U.S. Pat. No. 5,716,377, which is incorporated herein by reference. Systems for applying at least one pharmacological agent according to the methods described above are made up of one or more of the devices or components listed or incorporated by reference herein.

Devices and systems for applying at least one pharmacological agent to a subject and which may be adapted for use in the subject invention are described, e.g., in U.S. Pat. Nos. 7,363,076; 6,503,532; 5,302,395; 5,262,165; 5,248,501; 5,232,702; 5,230,896; 5,227,169; 5,212,199; 5,202,125; 5,173,302; 5,154,922; 5,139,786; 5,122,383; 5,023,252; 4,978,532; 5,324,521; 5,306,503; 5,302,395; 5,296,230; 5,286,491; 5,252,334; 5,248,501; 5,230,896; 5,227,169; 5,212,199; 5,202,125; 5,173,302; 5,171,576; 5,139,786; 5,133,972; 5,122,383; 5,120,546; 5,118,509; 5,077,054; 5,066,494; 5,049,387; 5,028,435; 5,023,252; 5,000,956; 4,911,916; 4,898,734; 4,883,669; 4,882,377; 4,840,796; 4,818,540; 4,814,173; 4,806,341; 4,789,547; 4,786,277; 4,702,732; 4,690,683; 4,627,429; 4,585,452; U.S. patent application Ser. Nos. 10/748,897; 10/748,976; 10/871,366; 10/846,486 10/917,270; 10/962,190; 11/060,643 11/251,629; 11/238,108; 11/592,027; 60/654,139; 60/702,776; and elsewhere, the disclosures of which are herein incorporated by reference.

Useful devices and systems may also include those associated with administering smelling salts (e.g., by inhalation), such as but not limited to e.g., those devices referred to as inhalers, inhalation therapy devices, diffusers, release vehicles, consciousness arousing devices, smelling salts applicators, smelling salts ampules, and the like. Related devices and systems that may be adapted for use in the herein described methods, systems and devices, include but are not limited to e.g., U.S. Patent Publication Nos. 2018/0221618, 2015/0080786, and 2014/0328884, 2005/0205685; and U.S. Pat. Nos. 9,527,623; 9,173,660; 5,948,399; 5,295,481; and 4,854,760; the disclosures of which are incorporated herein by reference in their entireties.

Devices and Systems for Applying Energy

Devices and systems for applying energy to a subject which may be adapted for use in the subject invention include embodiments configured to deliver energy using any of the methods described above. In accordance with the subject methods to apply energy to a subject, once operatively positioned, the energy applying device is activated to provide the relevant energy to the targeted area of the subject in a manner effective to practice the subject methods. Devices for applying energy to a subject include e.g., electrical energy application devices, vibrational energy application devices (e.g., ultrasonic energy application devices and infrasonic energy application devices), frequency specific application devices, light energy application devices, and the like Devices and systems for applying electrical energy to a subject which may be adapted for use in the subject invention include embodiments configured to deliver electrical energy using any of the methods described above. In accordance with the subject methods to apply electrical energy to a subject, once operatively positioned, the electric energy applying device is activated to provide an electrical signal to the targeted area in a manner effective to practice the subject methods.

A device for applying electrical energy to modulate autonomic function is an "electrical modulator". Electrical modulators may be positioned directly on a targeted area and may be implantable within the body of the subject or be wholly or partially external to the subject's body. An electrical energy applying device or system typically includes a stimulator such as one or more electrodes, a controller or programmer and one or more connectors for connecting the stimulating device to the controller.

The one or more electrodes employed in the subject devices are controllable to provide output signals that may be varied in voltage, frequency, pulse width, current and intensity. The energy source for the electrical output may be provided by a battery or generator that is operatively connected to the electrode(s). The energy source may be positioned in any suitable location such as adjacent to the electrode(s), or a remote site in or on the subject's body or away from the subject's body in a remote location and the electrode may then be connected to the remotely positioned energy source using wires. A controller or programmer may also be coupled with an electric energy applying device. The programmer is typically one or more microprocessors under the control of a suitable software program.

Devices and systems for applying vibrational energy to a subject which may be adapted for use in the subject invention include embodiments configured to deliver vibrational energy using any of the methods described above. In accordance with the subject methods to apply vibrational energy to a subject, once operatively positioned, the vibrational energy applying device is activated to provide the vibration to the targeted area in a manner effective to practice the subject methods.

A device for applying vibrational energy to modulate autonomic function is an "vibrational modulator". Vibrational modulators may be positioned directly on a targeted area and may be implantable within the body of the subject or be wholly or partially external to the subject's body. A vibrational energy applying device or system typically includes an applicator with one or more vibrational stimulators, a controller or programmer and one or more connectors for connecting the applicator to the controller.

The one or more applicators employed in the subject devices are controllable to provide output vibrations that may be varied in frequency, mode, intensity, power, impedance intensity, focusing, depth, pulsing, and duration. Applicators may in some instances include a transducer that transduces an electrical signal into the applied vibrational energy. The energy source for the vibrational output may be provided by a battery or generator that is operatively connected to the applicator(s). The energy source may be positioned in any suitable location such as adjacent to the applicator(s), or a remote site in or on the subject's body or away from the subject's body in a remote location and the applicator may then be connected to the remotely positioned energy source using wires. A controller or programmer may also be coupled with a vibrational energy applying device. The programmer is typically one or more microprocessors under the control of a suitable software program.

Devices and systems for applying vibrational energy to a subject which may be adapted for use in the subject invention include embodiments configured to deliver vibrational energy using any of the methods described above. In accordance with the subject methods to apply vibrational energy to a subject, once operatively positioned, the vibrational energy applying device is activated to provide the vibration to the targeted area in a manner effective to practice the subject methods.

A device for applying frequency specific energy to modulate autonomic function is an "frequency specific modulator". Frequency specific modulators may be positioned directly on a targeted area and may be implantable within the body of the subject or be wholly or partially external to the subject's body. A frequency specific energy applying device or system typically includes an applicator with one or more stimulators, a controller or programmer and one or more connectors for connecting the applicator to the controller. Frequency specific application devices include electrical energy application devices that operate within specific frequency bands as well as radio frequency application devices and the like.

The one or more applicators employed in the subject devices are controllable to provide output specific frequencies that may be varied in power, impedance intensity, focusing, depth, pulsing, and duration. Applicators may in some instances include a probe, an electrode, a pad, or the like. The energy source for the frequency specific output may be provided by a battery or generator that is operatively connected to the applicator(s). The energy source may be positioned in any suitable location such as adjacent to the applicator(s), or a remote site in or on the subject's body or away from the subject's body in a remote location and the applicator may then be connected to the remotely positioned energy source using wires. A controller or programmer may also be coupled with a frequency specific energy applying device. The programmer is typically one or more microprocessors under the control of a suitable software program.

Devices and systems for applying frequency specific energy to a subject which may be adapted for use in the subject invention include embodiments configured to deliver frequency specific energy using any of the methods described above. In accordance with the subject methods to apply frequency specific energy to a subject, once operatively positioned, the frequency specific energy applying device is activated to provide the frequency specific energy to the targeted area in a manner effective to practice the subject methods.

Devices and systems for applying light energy to a subject which may be adapted for use in the subject invention include embodiments configured to deliver light energy using any of the methods described above. In accordance with the subject methods to apply light energy to a subject, once operatively positioned, the light energy applying device is activated to provide the light to the targeted area in a manner effective to practice the subject methods.

A device for applying light energy to modulate autonomic function is a light energy application device and will generally include a light emitter. Light energy application devices may be positioned directly on a targeted area or within sufficient proximity of a targeted area. In some instances, a light emitter may be implantable within the body of the subject. In some instances, a light emitter may be wholly or partially external to the subject's body. A light energy applying device or system typically includes a light emitter and a controller or programmer. The light emitter may be operably connected to the controller, e.g., through one or more connectors for connecting the emitter to the controller or programmer or through a wireless connection. A light energy application device may include one or more optical components to control, condition, or otherwise modify the light energy emitted from the emitter before application to the subject. Useful optical components include but are not limited to e.g., lenses, filters, and the like.

The one or more light emitters employed in the subject devices are controllable to provide output light energy that may be varied in wavelength, intensity, duration, pulse length, and frequency. Light emitters may include an energy source that provides power to the light emitter to produce the light energy. The energy source for the light energy output may be provided by a battery or generator that is operatively connected to the light emitter(s). The energy source may be positioned in any suitable location such as adjacent to the light emitter(s), or a remote site in or on the subject's body or away from the subject's body in a remote location and the emitter may then be connected to the remotely positioned energy source using wires. A controller or programmer may also be coupled with a light energy applying device. The programmer is typically one or more microprocessors under the control of a suitable software program.

Devices and systems for applying light energy to a subject which may be adapted for use in the subject invention include embodiments configured to deliver light energy using any of the methods described above. In accordance with the subject methods to apply light energy to a subject, once operatively positioned, the light energy applying device is activated to provide the light energy to the targeted area in a manner effective to practice the subject methods.

In some embodiments, the device for applying energy includes a sensor for detecting a food allergy syndrome condition symptom and/or instigator. As used herein, an "instigator" is an aspect that causes or aggravates a food allergy syndrome condition and/or symptom. A sensor may take the form of an electrode or the like and may be configured specifically to detect one or more symptoms of a food allergy condition. Signals received by such a sensor may be amplified before further processing. A sensor may also take the form of a device capable of detecting nerve compound action potentials or may take the form of a transducer that includes an electrode with an ion selective coating applied which is capable of directly transducing the amount of a particular transmitter substance or its breakdown by-products. More detailed descriptions of sensors that may be employed in the practice of the subject invention, and other examples of sensors that may be employed are disclosed in U.S. Pat. No. 5,716,377, which is incorporated herein by reference. Systems for applying energy according to the methods described above are made up of one or more of the devices or components listed or incorporated by reference herein.

In embodiments in which energy is used, any suitable protocol may be used, where certain protocols include using an energy applying device to deliver a suitable amount of energy to a subject. Once an energy applying device is positioned in a suitable position on or about one or more targeted areas energy is applied thereto for a period of time sufficient to provide the desired effect.

A number of different devices and systems for applying electrical energy to a subject and which may be adapted for use in the subject invention are described, e.g., in U.S. Pat. Nos. 7,149,574; 7,711,430; 7,363,076; U.S. patent application Ser. Nos. 10/661,368; 10/748,976; 10/871,366; 10/846,486 10/917,270; 10/962,190; 11/060,643 11/251,629; 11/238,108; 11/592,027; 60/654,139; and 60/702,776; and elsewhere, the disclosures of which are herein incorporated by reference.

A number of different devices and systems for applying TENS energy to a subject and which may be adapted for use in the subject invention are described, e.g., in U.S. Pat. Nos. 7,200,443 and 8,428,738; as well as U.S. Patent Publication Nos. 2016/0310315 and 2018/0117017; and elsewhere, the disclosures of which are herein incorporated by reference.

A number of different devices and systems for applying ultrasonic energy to a subject and which may be adapted for use in the subject invention are described, e.g., in U.S. Pat. Nos. 5,413,550, 7,283,861, and 8,715,209; as well as U.S. Patent Publication Nos. 2011/0112394, 2011/0130615, 2011/0178442, 2011/0208094, 2017/0080255, 2012/028350, 2011/0190668, 2014/0343463, and 2007/0203432; and elsewhere, the disclosures of which are herein incorporated by reference.

A number of different devices and systems for applying infrasonic energy to a subject and which may be adapted for use in the subject invention are described, e.g., in U.S. Pat. Nos. 8,517,911, 9,457,166, 9,480,812; as well as U.S. Patent Publication Nos. 2007/0203432, and 2016/0262974; and elsewhere, the disclosures of which are herein incorporated by reference.

A number of different devices and systems for applying frequency-specific modulation energy to a subject and which may be adapted for use in the subject invention are described, e.g., in U.S. Pat. Nos. 9,808,641, 10,010,713, 10,155,114; as well as U.S. Patent Publication No. 2019/0001135; and elsewhere, the disclosures of which are herein incorporated by reference. Useful devices, and components thereof, for frequency specific modulation, that may be adapted for use herein, also include those employing radio frequency (RF) modulation, such as but not limited to e.g., the Abbott NT2000iX™ RF Generator and Simplicity™ probe.

A number of different devices and systems for applying light energy to a subject and which may be adapted for use in the subject invention are described, e.g., in U.S. Pat. Nos. 950,189; 9,610,022; 9,696,804; 9,717,904; 9,782,221; 9,833,276; 9,968,541; 9,919,162; 9,993,661; 10,111,729; 10,118,049; 10,149,975; 10,155,121; 10,183,174; 10,188,872; 10,219,944; 10,252,077; 10,252,078; and RE47,266; and elsewhere, the disclosures of which are herein incorporated by reference.

Devices of the present disclosure may include various components including but not limited to e.g., one or more components of one or more of the modulation devices described herein, user-interface components, input sensors, biofeedback components, memory components, computer readable media components, and the like.

As used herein "user-interface components" generally refers to components of a device that may deliver, receive, or deliver and receive input and/or output to a user of a device. Useful user interfaces include but are not limited to e.g., a display (e.g., a series of indicator lights, a monitor, a screen, a projector, a virtual reality headset, etc.), an auditory device (e.g., a buzzer, a speaker, headphones, etc.), a tactile stimulator (e.g., a vibration device, a probe, etc.), and the like. Such components of a user interface may be communicably connected, either unidirectionally connected or bidirectionally connected, to a computing device of the system by wired or wireless means. With respect to the user, a user-interface may be uni- or bidirectional. For example, in some instances, a bidirectionally user-interface employed may be a touch screen. In some instances, a unidirectional user-input employed may be a screen including e.g., a graphical user interface.

User interfaces may include one or more components for user input. In some embodiments, the user input device may include a joystick, a controller, a steering wheel, a lever, a button, a touchscreen, a keyboard, a gamepad, a mouse, a trackball, a stylus, a wand, a handheld device, a wearable device, a biometric device, and the like. User input devices are not limited to tactile input and may in some instances include user input devices for auditory input (e.g., a microphone) or movement input (e.g., eye-movement tracking devices).

In some instances, a device of the present disclosure may include a multimedia device. Useful multimedia devices include devices consisting of goggles to be worn by the user, LCD screen, earphones, loudspeakers and combinations thereof.

Biofeedback components may employ one or more user interface devices or components thereof, including e.g., a computer screen or other visual display. Biofeedback may be provided via text, graphics, colors, sounds and the like. In some instances, in pace of or in addition to visual biofeedback, audio and/or voice instruction may be employed.

As a non-limiting example, in some embodiments, a subject may be treated for a food allergy condition using a device configured to provide biofeedback to the subject relating to the state of the subject's autonomic nervous system. For example, the device may include at least one input sensor that measures a readout from the subject's autonomic nervous system and provides biofeedback to the subject to directly or indirectly induce a behavioral modulation to treat the subject for the food allergy condition. Useful readouts may include readouts from electrical (e.g., ECG) or optical (e.g., PPG) or other biophysical (e.g., carbon dioxide levels, oxygen saturation levels, glucose levels, and the like) sensors. Useful biofeedback may include direct autonomic nervous system feedback (e.g., a score relating the sympathetic/parasympathetic balance of the subject, or the like) or indirect feedback (e.g., a visual, auditory or sensory indication to change breathing rate, or the like). For example, in some embodiments, a device may measure a subject's HRV and induce the subject to modulate the subject's breathing rate based on the measured HRV. In some instances, HRV monitoring may be continued and the device may continue to induce changes in breathing rate based on the measured HRV. As another sample, in some embodiments, a device may measure a subject's carbon dioxide levels, oxygen saturation levels, and the like, with or without additional measurements such as HRV, and induce the subject to modulate the subject's breathing rate based on the measured input(s). In some instances, carbon dioxide and/or oxygen saturation monitoring may be continued and the device may continue to induce changes in breathing rate, e.g., based on the measured carbon dioxide and/or oxygen saturation level, and optionally other measured parameters.

Devices of the present disclosure employing biofeedback components may configured as a single contained device or may involve a system of separate components, such as e.g., a system with a separate sensor and controller. In some instances, the controller of a biofeedback component of a subject device may be a mobile phone or other personal electronic device with sufficient processor power to provide the necessary processing functions. Biofeedback devices, and components thereof, that may be adapted for use in devices, systems and methods of the present disclosure include but are not limited to e.g., those described in U.S. Pat. Nos. 8,298,131; 8,428,702; 10,092,206; 10,175,254; 10,188,345; and U.S. Patent Publication Nos. 2010/0174205 and 2012/0116176; the disclosures of which are incorporated herein by reference in their entireties.

In some instances, devices and systems of the present disclosure may employ one or more input sensors that affixed and/or reversibly attached to a subject. Such sensors may serve to detect one or more aspects of the autonomic nervous system, including e.g., where such an aspect is a bioelectrical signal, such as a signal associated with HRV, carbon dioxide levels, oxygen saturation levels, glucose levels, or the like. For example, and HRV input sensor may be employed in some instances to measure and assess parasympathetic bias. Affixed input sensors may be surgically or otherwise attached to a subject. Reversibly attached input sensors may be placed in contact with a user in such a manner as the device is in sufficient contact for sensing the desired aspect of the subject's autonomic nervous system, and may also be readily removed and/or reattached as desired. Reversibly attached devices include but are not limited to "wearable" devices, nonlimiting examples of which include wristbands, wristwatches, earpieces, eyewear (e.g., glasses, etc.), neck-ware and jewelry (e.g., necklaces, collars, earrings, etc.), footwear, and the like. As a nonlimiting example, input sensor-containing devices may be a wristband or wristwatch configured with one or more sensors that, when the device is activated, cause the wristband or wristwatch to perform the sensing function.

In some embodiments, a device of the present disclosure may include one or more input sensors and one or more energy application components. Such devices may be configured such that the modulation of the subject's autonomic nervous system is integrated with the input from the sensor. Accordingly, in some instances, devices that include both input-receiving and modulation-generating functions may operate in a closed-loop manner. In some instances, a device a device having both input-receiving and modulation-generating functions may be operated in an open-loop manner, as desired. Useful input sensors include but are not limited to e.g., biometric sensors such as e.g., electrocardiography sensors, photoplethysmogram sensors, electroencephalogram sensors, carbon dioxide sensors, oxygen saturation level sensors, glucose level sensors, and the like, and the like. In some instances, devices, systems and methods of the present disclosure may make use of a combination of sensors, including e.g., two or more of an electrocardiography sensor, a photoplethysmogram sensor, an electroencephalogram sensor, a carbon dioxide sensor, an oxygen saturation level sensor, and a glucose level sensor.

Sensors may be configured to contact any convenient and appropriate area of a subject, including but not limited to e.g., a finger, an ear, a neck area, a wrist area, an arm area, a leg area, a chest area, a head or scalp area, a mouth area, a lip, a nose area, and the like. As summarized above, in some instances, sensors may be implanted, wholly or partially, within a subject.

Devices, systems and methods of the present disclosure may include one or more computer readable mediums associated therewith. Computer readable mediums may include non-transitory computer readable media including instructions stored thereon for causing a computer device/system to implement the methods of the present disclosure, including any embodiments of the methods described elsewhere herein. Non-transitory physical computer readable media of the present disclosure include, but are not limited to, disks (e.g., magnetic or optical disks), solid-state storage drives, cards, tapes, drums, punched cards, barcodes, and magnetic ink characters and other physical medium that may be used for storing representations, instructions, and/or the like.

The following examples are offered by way of illustration and not by way of limitation.

EXPERIMENTAL

We performed extensive autonomic testing on a 5-year-old subject with a history of virally-triggered asthma and severe tree nut allergy. The subject's heart rate was measured during deep breathing. During inhalation, activation of lung stretch receptors normally suppresses vagal activity, promoting tachycardia. The subject's heart rate during inhalation was 104 beats per minute, which is normal for a 5-year-old. During exhalation, unloading of lung stretch receptors reverses vagal suppression, typically reducing heart rate by 20 to 30 beats per minute (bpm). The subject's heart rate declined to 54 bpm, suggesting sympathetic underactivity. Heart rate response to $CO_2$ retention and release did not alter heart rate variability, suggesting central autonomic dysfunction, possibly at the brain stem level. Large fiber autonomic neuropathy was ruled out through additional testing. Skin sympathetic response (SSR) tests were performed limb-to-limb to localize the autonomic dysfunction. Delayed sympathetic function was observed only between the upper limbs, suggesting a possible defect somewhere along the cervico-thoracic sympathetic arc.

The findings appear consistent with the subject's history of asthma (characterized by expiratory wheeze and bronchospastic cough) and food allergy syndrome (anaphylaxis, angioedema, gastrointestinal cramping, hypotension, and bronchospasm). In the case of asthma, an allergic response to a viral antigen (characterized by degranulation, release of substance P, and activation of other cascading pathways) activates the autonomic afferent fibers, which are biased towards vagal dominance in this subject. During exhalation, insufficient sympathetic counter-response to vagal resurgence (associated with unloading of lung stretch receptors) results in expiratory wheeze (bronchoconstriction) and asthmatic cough (bronchospasm). In the case of food allergy syndrome, an allergic response to tree nut antigen (characterized by degranulation, release of vasoactive intestinal peptide, and activation of other pathways) triggers autonomic afferents.

Given the subject's underlying vagal bias, the subject exhibits symptoms consistent with vagal overload including angioedema, bronchoconstriction, hypotension, and gastrointestinal cramping. These are all hallmarks of anaphylaxis. The underlying autonomic dysfunction effectively turns a routine immunologic response to an antigen into a catastrophic, maladaptive response.

In the case of our 5-year-old subject, the origin of the subject's sympathetic under-responsiveness remains to be explored. Possible defect locations include end-organs, afferent fibers, brain stem, hypothalamus, spinal cord, and efferent fibers. Since the autonomic dysfunction appears regional, a genetic or cellular defect seems less likely, although secondary systemic consequences to the autonomic nervous system from chronic use of beta-agonists and steroids should be considered. There is a classic allergic reaction characterized by hyperreactivity of the respiratory and GI mucosa with type I hypersensitivity and provocative exposure leading to eosinophilia, plasma cells, and degranulated mast cells. The observations indicate that a vasomotor adjunct with an imbalance in ANS input results in the vasomotor, cardiovascular, and inflammatory anaphylaxis responses. The disease is characterized by the classic mismatch of parasympathetic over sympathetic drive of swelling, flushing, smooth muscle spasms, arterial spasm, and diarrhea.

All publications and patent applications mentioned in this specification are herein incorporated by reference to the same extent as if each individual publication or patent application was specifically and individually indicated to be incorporated by reference.

The invention now being fully described, it will be apparent to one of skill in the art that many changes and modifications can be made thereto without departing from the spirit and scope of the appended claims.

What is claimed is:

1. A method of treating a human subject for an abnormal parasympathetic bias mediated condition, the method comprising:
   modulating, via a wristband comprising an energy application component, at least a portion of the human subject's autonomic nervous system to increase the sympathetic/parasympathetic activity ratio in a manner effective to treat the human subject for the abnormal parasympathetic bias mediated condition, wherein:
   the energy application component comprises a vibrational stimulator configured to apply vibrational energy to the subject's autonomic nervous system;
   the human subject is known to have an abnormal parasympathetic bias; and
   increasing the sympathetic/parasympathetic activity ratio comprises decreasing parasympathetic activity.

2. The method according to claim 1, wherein the parasympathetic bias mediated condition is an acute condition.

3. The method according to claim 2, wherein the parasympathetic bias mediated condition is a predicted adverse response to a stimulus.

4. The method according to claim 3, wherein the stimulus is nutritional ingestion.

5. The method according to claim 4, wherein the parasympathetic bias mediated condition is a food allergy syndrome condition.

6. The method according to claim 1, further comprising increasing sympathetic activity.

7. The method according to claim 1, further comprising employing a paradoxical protocol to modulate the sympathetic/parasympathetic activity ratio, wherein the paradoxical protocol comprises applying an appropriate stimulus to the subject to initially decrease the sympathetic/parasympathetic activity ratio of the subject after which the subject is permitted to mount a compensatory response comprising an increase in the sympathetic/parasympathetic activity ratio of the subject.

8. The method according to claim 1, wherein the subject is known to have vagal bias.

9. The method according to claim 8, wherein the vagal bias is characterized by one or more of vagal dominance, vagal hypersensitivity and sympathetic insufficiency.

10. The method according to claim 1, wherein the method further comprises determining whether the subject has parasympathetic bias.

11. The method according to claim 1, further comprising the administration of smelling salts.

12. The method according to claim 1, wherein the sympathetic/parasympathetic activity ratio is modulated via biofeedback, the biofeedback comprising:
   assessing the sympathetic/parasympathetic balance of the human subject; and
   providing to the human subject a direct indication of the assessment.

13. The method according to claim 12, wherein assessing the sympathetic/parasympathetic balance of the human subject comprises measuring heart rate variability (HRV).

14. The method according to claim 12, wherein assessing the sympathetic/parasympathetic balance of the human subject comprises measuring carbon dioxide levels.

15. The method according to claim 12, wherein the direct indication of the assessment is provided to the human subject via a personal electronic device.

16. The method according to claim 1, wherein the vibrational energy is ultrasonic energy.

17. The method according to claim 1, wherein the vibrational energy is infrasonic energy.

* * * * *